(12) United States Patent
Bauche et al.

(10) Patent No.: US 9,657,311 B2
(45) Date of Patent: May 23, 2017

(54) LENTIVIRAL VECTORS CONTAINING AN MHC CLASS I, MHC CLASS II, OR B2 MICROGLOBULIN UPSTREAM PROMOTER SEQUENCE

(71) Applicant: THERAVECTYS, Villejuif (FR)

(72) Inventors: Cecile Bauche, Paris (FR); Emeline Sarry, Malakoff (FR)

(73) Assignee: THERAVECTYS, Villejuif (FR)

( * ) Notice: Subject to any disclaimer, the term of this patent is extended or adjusted under 35 U.S.C. 154(b) by 0 days.

(21) Appl. No.: 14/287,699

(22) Filed: May 27, 2014

(65) Prior Publication Data

US 2014/0356946 A1  Dec. 4, 2014

(30) Foreign Application Priority Data

Jun. 3, 2013  (EP) .................................. 13305738

(51) Int. Cl.
*C12N 15/86* (2006.01)

(52) U.S. Cl.
CPC .... *C12N 15/86* (2013.01); *C12N 2740/16043* (2013.01); *C12N 2830/30* (2013.01); *C12N 2830/85* (2013.01)

(58) Field of Classification Search
None
See application file for complete search history.

(56) References Cited

U.S. PATENT DOCUMENTS

| 2007/0037165 A1* | 2/2007 | Venter et al. ..................... 435/6 |
| 2014/0120132 A1 | 5/2014 | Bauche et al. |
| 2014/0134195 A1* | 5/2014 | Russell ....................... 424/184.1 |

FOREIGN PATENT DOCUMENTS

| WO | 2009/019612 A2 | 2/2009 |
| WO | 2011/138251 A2 | 11/2011 |
| WO | 2013/046034 A2 | 4/2013 |

OTHER PUBLICATIONS

Richardson et al., Intrabody-mediated knockout of the high-affinity IL-2 receptor in primary human T cells using a bicistronic lentivirus vector; Gene Therapy, vol. 5, pp. 635-644, 1998.*
Okada et al., Targeted Gene Modification in Mouse ES Cells Using Integrase-Defective Lentiviral Vectors; Genesis, vol. 47, pp. 217-223, 2009.*
Kumar et al., Systematic determination of the packaging limit of lentiviral vectors; Human Gene Therapy, vol. 12, pp. 1893-1905, 2001.*
Horton et al., Gene map of the extended human MHC; Nature Reviews Genetics, vol. 5, pp. 889-899, 2004.*
LeibundGut-Landmann et al., Specificity and expression of CIITA, the master regulator of MHC class II genes; Eur. J. Immunol, vol. 34, pp. 1513-1525, 2004.*
Van Den Elsen P J et al: "Transcriptional regulation of antigen presentation", Current Opinion in Immunology, vol. 16, No. 1, Feb. 1, 2004, pp. 67-75.
Israel A et al: "Two Purified Factors Bind to the Same Sequence in the Enhancer of Mouse MHC Class I Genes One of Them is a Positive Regulatory Induced Upon Differentiation of Teratocarcinoma Cells", Nucleic Acids Research, vol. 17, No. 13, Jan. 1, 1989, pp. 5245-5258.
Namhoon Lee et al: "Three Novel Downstream Promoter Elements Regulate MHC Class I Promoter Activity in Mammalian Cells", Plos One, vol. 5, No. 12, Dec. 13, 2010, p. e15278.
Shatrah Othman et al: "Induction of MHC Class I HLA-A2 promoter by dengue virus occurs at the NFB binding domains of the Class I Regulatory Complex", Virus Research, vol. 163, No. 1, Sep. 30, 2011, pp. 238-245.
European Patent Office, European Search Report, European Appln. No. EP 13305738.0, Nov. 25, 2013.
Todd Evans et al: "Control of Globin Gene Transcription", Annual Review of Cell Biology, vol. 6, pp. 95-124, 1990.
Peter J. Van Den Elsen et al: "Expression Regulation of Major Histocompatibility Complex Class I and Class II Encoding Genes", Frontiers in Immunology, vol. 2, article 48, 2011-10.
Rebecca L Tallmdge et al: "Characterization of the Beta2-microglobulin Gene of the Horse", Immunogenetics, vol. 54, pp. 725-733, 2003.

* cited by examiner

*Primary Examiner* — Addison D Ault
(74) *Attorney, Agent, or Firm* — Whitham, Curtis & Cook, P.C.

(57) ABSTRACT

The present invention relates to the insertion of an MHC class I, MHC Class II, or β2 microglobulin upstream promoter sequence into a lentiviral vector to increase viral titers. The invention encompasses these vectors, methods of making the vectors, and methods of using them, including medicinal uses.

21 Claims, 13 Drawing Sheets

```
Upstream B2m       (1)  AGAAGTTCTCCTTCCTGCTAGGTAGGATTCAAAGATCTTAATCTCTCGGGTTTCGGTTTCTCGAATGAAAAATGCAGGTCCGAGCAGTTAACTGGCGGGG
Upstream HLA-E     (1)  --------------------------------------------------CTGGAGGGCAATGCACGATCTTGGCTCACGTTCCCCAACCTCTGCCTCAGCC
Upstream HLA-B7    (1)  --------------------------------------------------ACTCTCGGCACAGTTCCCCTGTCCCGGTCACTCCCTACACAAAGAGTCAAG-AGGAGAGTAAGGAGTGGGA-GGCAGGG
Upstream HLA-C     (1)  --------------------CAAGGGAGAGGTAAGCTGTCCTTTATTTGCTGGATGTAGTTAATTACCTGAGGT---A-AGGTAAGGCAAAGAGTGGGA-GGCAGGG
Upstream HLA-F     (1)  --------------------TTCAATGTCTGCACCAACAAGCTCCTGGGGTGAATTTCTTCCAAAAGAGTCCGGGGAGTCCAGGTATGGAATGGGA-GGCAGAA
Upstream HLA-G     (1)  --------------------GCCTCACTCTCTGCCAACAAGTCCATGGGATGATTGATTTTCTTCTAGAAGAGAGTCCAGG-AGGACAGGTAAGGAGTGGGA-GGCAGGG
Upstream HLA-A2    (1)  --------------------------------------------------TGGACAGGTAAGGAGTCCAGG-TGGACAGGTAAGGAGTGGGA-GTCAGGG
Consensus          (1)                                                      G   T A T TCTGGCA CAA CTCC TGGG TGAGTT CTCTACAAGAG CCA  G AGGACAGGTAAGGAGTGGGA GGCAGGG Upstream B2m     (101)  GCACCATTAGCAAGTCACTTAGCCATCTCTCGCGCCACAGTCTGCAAAGCCCACAG---CCTTAATGCCTCCCAGCCTGAAGCTCTAGAATGACCGCC
Upstream HLA-E    (76)  TCCCAAGTAGCCAGGATTACAGCCAGGATCAGCCGCCACCAGGCGCCTAATTTTTGGACTTTTTAGTAGAGACAGGGTTCTTCCATA--TTGGTCGGGCTGGTCT
Upstream HLA-B7   (80)  AGTCCAGTT-C-AGGG---ACAGGGATTCCAGGA---ACAGGGATTCCAGGA--GAAGTGAAGGGGAAGTGCGGCGAGAAGTGGGGCAGCTGGGGCCAGGC-GGGGTCCAGCCTGGGGTCCTGCCAGCCTGGGGTCCACAGACAG--AT
Upstream HLA-C    (87)  AGTCCAGTT-C-AGGG---ACGGGGATTCCAGGA---GAAGTGAAGGGGAAGGAGGGGAAAGTCGGCCATGGCCAAGGTTTTTCCCTGGTTTCT-CAGCC-----
Upstream HLA-F    (84)  AGTTCCAAT--CAAGGG---ACTGGGGATTTCGGAATGAATTGAATAAATGAAAGGGAGAGAAGGGAAAGTGGGGTTCTCCCTGGTTTCT-CAGACAG--CT
Upstream HLA-G    (84)  AGTCCAGTT-C-AGGG---ACAGGGATTCCGGGATGCAAAAGTGAAGGGAGGAGCGCCCAGGGACCTTGCCGAGGGTTCTCCCTGGTTCT-CAGAGCAG--CT
Upstream HLA-A2   (84)  AGTCCAGTT--CCAGGG---ACAGAGATTAGGGGATAAAAAGTGAAAGGCAGGGGCCCCATGCCCAGGCCCATGCCCGAGGGTT-TCTCCCTTGTTCT-CAGACAG--CT
Consensus        (101)  AGTCCAGTT C AGGG   ACAGGGA TTCCGGGA  AGAAGTGAAGGGA   AGGG CTGGG CCAT C GAGGGT TCTCCCTGGTTTCT CAGACAG  CT Upstream B2m     (198)  CGGTGTCCCAGCTGGGGCGCGCACCC----CAGATC---GGAGGGCGCCGA-TGTACAGA---CACCAAACTCACCCAGT--CTAGTCCATGCCTTCTTA
Upstream HLA-E   (174)  CGAACTCCCCAGACCTCAGGTGATCAGCCCGCTGGCCTCCCAAAGTGCTGAGATTACAGGCGTGAGATTACAGCGTGAGATTACAGGCGTGAGATTACAGGC-C-CAGGACTAATTCTAA
Upstream HLA-B7  (174)  CCTTGTCCAGACTCCAGGACACAGTGTGACAAAGA-G-GCTTGGTGTAGG-AGAAGAGGGATCAGGACAGGAGGATCAGGACAGAAGTCCAGGTCC-CCGACGG-GGCTTTCA
Upstream HLA-C   (178)  CCTTGGCCAGACTCCAGGACACAGTGTGACAAAGA-T-GCTTGGTGTAGG-AGAAGAGGGATCAGGACGGAAGTCCAGGTCC-CCGGGCGG-GGTTCTCA
Upstream HLA-F   (173)  CCCGGCCGAAATCTCAGGGAGGAGACATTGAGACACCCT-GCACAGAGGTGGAGCGGGAAGTCCAGGGCAAAGTCCAGGGCAAAGTCCAGGGCAAAGTCCAGGGCAAGTGCAGGCCAAAG-GCTCTCA
Upstream HLA-G   (177)  CCTGGGCCAAGACTCCAGGGAGAGACACTGAGACGAAC---GCTTCGGCACAAG-AGTAGCGGGGTCAGGGCCGAAG-CC-AGGGCCCCAGGCGGTTGGCTCTCA
Upstream HLA-A2  (178)  CTTGGGCCAAGACTCCAGGGAGAGACATTGAGACAGAGG---GCTTGGCACAGA-AGCAGAGGGGTCAGGGGTCAGGGCGAAG-CC-AGGGCCCCAGGCGGTGGCTCTCA
Consensus        (201)  CCT GGCCAAGACTCAGG AGACA TG GACA AGC     GCTGG GCAGG AG AGAGGGGTCAGG  CGAAGTCCAGG  CC  CAGCCGT  GGCTCTCA Upstream B2m     (286)  AACA-TCACGAGACTC----                                  (SEQ ID NO:1)
Upstream HLA-E   (270)  GAGTGTGCAGATACCGAAACCTAAAAGTT---                      (SEQ ID NO:2)
Upstream HLA-B7  (269)  GGCTCTC---ACGCTCCGACGGCGTCTG---                       (SEQ ID NO:3)
Upstream HLA-C   (273)  GGGTCTC---AGGCTCCAAGGGCCGTGTCTG---                    (SEQ ID NO:4)
Upstream HLA-F   (271)  AGGGCTC---AGCCCCCC--AGCCGGTGCTCGGG---                 (SEQ ID NO:5)
Upstream HLA-G   (272)  GGGTCTC---AGGCCCCACAGGCGGTGTATGG---                   (SEQ ID NO:6)
Upstream HLA-A2  (273)  GGGTCTC---ACGGGCCGAAGGGGGGTGATG---                    (SEQ ID NO:7)
Consensus        (301)  GGGTCTC  AGGC CCGAAGGC GTGT TG                        (SEQ ID NO:8)
```

```
                                                                                                                    Y
CCAGTTCTCACTCCC┌ATTGG┐TGTCGGGTTTCCAGAGAAGCCAATCAGTGTCGTCGGGG-TCGCGGTTCTAAAGTCCCACGGACCCACCGGGACTCA-GATTCTCCCAGACGCCGAGG  SEQ ID NO:37
CCACTTCCCACTCCC│ATTGG│TATTGG TATTGGATATCTACAGAGAAGCCAATCAGCGTCCCGCCCGG-TCCCAGTTCTAAAGTCCCACGCACCCCGACTCA-GAG              SEQ ID NO:38
TCAGTTCTCATTCCC│AATGG│TGTCGGGTTCTGGGTTCTAGAGAAGCCAATCAGCGTCGCCAGACTCCGACTATABAGTCC------CCATCGGACTCAAGAAGTTCTCAGGACTCAGAGG SEQ ID NO:39
               │     │
TGCGGGCCCTTGTCC│TNNATTGG│CACGCGTTAATAAGTGGAGGCGTCGCGCTGGGGCATTCTGAAGCTGAGCAGCATTCGGGCCGAG                              SEQ ID NO:40
               │     │
TCAAAATATTTTTCT│GATTGG│CAAAGAGTAATTGATTTGCATTTAATGGTCAGAGACTCTATTACACCCCACACTCTCTTTCTTTATTCTTGTCTGTTCTGCCCTCACTCCCGAGCT SEQ ID NO:41
               └─────┘

LENTIVIRAL VECTORS CONTAINING AN MHC CLASS I, MHC CLASS II, OR B2 MICROGLOBULIN UPSTREAM PROMOTER SEQUENCE

TECHNICAL FIELD

The present invention is in the field of recombinant vaccine technology and relates to improvements of lentiviral vectors, which can be used as therapeutic and prophylactic vaccines. The vectors containing MHC class I, MHC Class II, or β2 microglobulin upstream promoter sequences provide improved characteristics over other vectors.

BACKGROUND

Recombinant vaccines have been developed with the progress of recombinant DNA technology, allowing the modification of viral genomes to produce modified viruses. In this manner, it has been possible to introduce genetic sequences into non-pathogenic viruses, so that they encode immunogenic proteins to be expressed in target cells upon infection, in order to develop a specific immune response in their host.

Such vaccines constitute a major advance in vaccine technology (Kutzler et al., *Nat Rev Genet*, 9(10): 776-788, 2008). In particular, they have the advantage over traditional vaccines of avoiding live (attenuated) virus and eliminating risks associated with the manufacture of inactivated vaccines.

Gene delivery using modified retroviruses (retroviral vectors) was introduced in the early 1980s by Mann et al. (*Cell*, 33(1):153-9, 1983). The most commonly used oncogenic retroviral vectors are based on the Moloney murine leukemia virus (MLV). They have a simple genome from which the polyproteins Gag, Pol and Env are produced and are required in trans for viral replication (Breckpot et al., 2007, *Gene Ther*, 14(11):847-62; He et al. 2007, *Expert Rev vaccines*, 6(6):913-24). Sequences generally required in cis are the long terminal repeats (LTRs) and its vicinity: the inverted repeats (IR or att sites) required for integration, the packaging sequence ψ, the transport RNA-binding site (primer binding site, PBS), and some additional sequences involved in reverse transcription (the repeat R within the LTRs, and the polypurine tracts, PPT, necessary for plus strand initiation). To generate replication-defective retroviral vectors, the gag, pol, and env genes are generally entirely deleted and replaced with an expression cassette.

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, *Expert Rev vaccines*, 6(6):913-24), allowing antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, *J Gen Virol*, 70(7):1617-39). They have the same basic organization as all retroviruses, but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

The design of recombinant integrative lentiviral vectors is based on the separation of the cis- and trans-acting sequences of the lentivirus. Efficient transduction in non-dividing cells requires the presence of two cis-acting sequences in the lentiviral genome, the central polypurine tract (cPPT) and the central termination sequence (CTS). These lead to the formation of a triple-stranded DNA structure called the central DNA "flap", which maximizes the efficiency of gene import into the nuclei of non-dividing cells, including dendritic cells (DCs) (Zennou et al., 2000, *Cell*, 101(2) 173-85; Arhel et al., 2007, *EMBO J*, 26(12): 3025-37).

Dendritic cells are of primary importance for antigen presentation because they constitute the main class of antigen presenting cells (APCs) whose primary function is to present antigens and initiate an immune response.

To generate an immune response, antigenic proteins must be processed by cells into peptides that are displayed on the cell surface by major histocompatibility complex proteins (MHCs). Circulating APCs present the peptide-MHC complexes to T cells in the draining lymph nodes, where they interact with T cell receptors, and, in conjunction with co-stimulatory signals, activate the T cells.

A variety of studies have shown that inoculation with lentiviral vectors leads to antigen presentation by DCs and strong activation of antigen specific cytotoxic T lymphocytes (CTLs; CD8$^+$ T cells). Therefore, lentiviral vectors have been engineered for gene transfer and immunotherapy applications.

Lentiviral vectors have been improved in their safety by removal of the LTR U3 sequence, resulting in "self-inactivating" vectors that are entirely devoid of viral promoter and enhancer sequences originally present within the LTRs.

The lentiviral particles, which contain lentiviral vectors, can be produced by recombinant technology upon transient transfection of HEK 293T human cultured cells by different DNA plasmids:

(i) a packaging plasmid, which expresses at least the Gag, Pol Rev, Tat and, in some cases, structural and enzymatic proteins necessary for the packaging of the transfer construct;

(ii) a transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection.

Non-integrative lentiviral vectors have designed in an attempt to mitigate the risks of potential oncogenesis linked to insertional mutagenesis events, particularly for vaccination purposes.

In vaccination based on direct injection of antigen-encoding integrative lentiviral vectors, transduced cells expressing the relevant antigen become targets of the elicited immune response and are eliminated within a few days or weeks from the vaccinated organism.

In addition, deletion in the U3 region of the 3' LTR of the viral promoter and enhancer sequences in self-inactivating lentiviral vectors limits the likelihood of endogenous promoter activation. This deletion directly addresses the experiences gained from the SCID-X1 gene therapy trial carried out in 1998-1999, performed with Moloney virus-based retroviral vectors on children suffering from a rare form of X-linked (SCID-X1 gene) severe immunodeficiency disease (Cavazzana-Calvo et al., 2000, *Science.*, 288(5466):669-72). During this trial, four of nine children developed leukemia as a result of the integration of the Moloney-derived retroviral vector at close proximity to the human LM02 proto-oncogene (Hacein-Bey-Abina et al., 2008, *J. Clin. Invest.*, 118(9):3132-3142). It was demonstrated that malignancy was the consequence of the proximity of the viral U3 promoter/enhancer to the LM02 proto-oncogene.

Enhancers are cis-acting sequences, which can act as transcriptional activators at a distance. They have been widely employed in viral derived vectors because they appear to be the most efficient for obtaining transgene strong expression in a variety of cell types, in particular DCs (Chinnasamy, Chinnasamy et al., 2000, Hum Gene Ther 11(13):1901-9; Rouas et al., 2008, *Cancer Gene Ther* 9(9): 715-24; Kimura et al., 2007, *Mol Ther* 15(7):1390-9; Gruh et al., 2008, *J Gene Med* 10(1) 21-32). However, given the safety issue of insertional mutagenesis, such transcriptional enhancer sequences should be deleted from the lentiviral vector constructs to abolish the risk of insertional mutagenesis by enhancer proximity effect. This enhancer proximity effect is by far the most frequent mechanism of insertional mutagenesis and is the only effect described in human or animal cases of tumorigenic events after gene transfer.

Thus, there is a need to develop retroviral, particularly lentiviral vectors, which do not include viral enhancers and which allow sufficient expression of transgenes encoding immunogenic peptides, if possible as much expression as that observed when using the CMV promoter. Particularly, there is a need for vectors with improved titers.

A study has reported on the replacement of viral promoters by DC-specific promoters deriving from major histocompatibility complex class II genes (MHC class II) (Kimura et al., 2007, *Mol Ther* 15(7):1390-9) and dectin-2 genes (Lopes et al., 2008, *J Virol* 82(1):86-95). The dectin-2 gene promoter used in Lopes et al. contains a putative enhancer and an adenoviral conserved sequence (inverted terminal repeats in adenovirus promoter) (Bonkabara et al., 2001, *J. Immunology*, 167:6893-6900). The MHC class II gene promoter used by Kimura et al. does not contain any known enhancer.

Yet, without an enhancer, the MHC class II promoter was found not to provide sufficient transgene expression in DCs. In particular, lentiviral vectors including MHC class II promoters did not provoke an immune reaction in immunocompetent C57BL/6 mice, in contrast to the immune responses observed with CMV promoters/enhancers. Although integration and persistent transgene expression were observed after injection in mice, the lentiviral vectors transcribed through MHC class II promoters failed to stimulate an antigen-specific CD8+ cytotoxic T-lymphocyte response, even after vaccination boost. The authors of these studies therefore concluded that the use of MHC class II promoters was of interest only for applications where persistence of expression is sought as in gene replacement therapy, but not in the context of immunotherapy.

Thus, the MHC class II promoter is not an adequate promoter for lentiviral vectors for induction of an immune response against an antigen. Moreover, the dectin-2 promoter is dendritic cell specific, which does not allow elimination of vectors that are integrated into other non-expressing cell types. Moreover, the dectin-2 promoter appears to contain an enhancer. Thus, the dectin-2 promoter is not a good promoter for lentiviral vectors for safety reasons.

Preferably, in immunotherapy, lentiviral vectors provide effective expression of the transgene that elicits a desired specific immune response. This requires that the expression is at a high level in APCs, such as dendritic cells.

It is also preferable that the cells transduced by the lentiviral vectors are eliminated by the immune response to provide a higher degree of safety. That is, the immune response generated against the transgene can elicit an immune response in the host sufficient to eliminate the cells that are transduced by the lentiviral vectors. The elimination of transduced cells eliminates the persistence of the lentiviral vector in the host, and possible secondary effects of the vector. In order for the transduced cells to be eliminated, expression is required in non-dendritic cells at a level that allows elimination by the immune response.

At the same time, the promoter should maximize immune stimulation through the key cells (i.e., dendritic cells) involved in the activation of naïve and memory T cells, and should minimize the risk of insertional mutagenesis and genotoxicity in stem cells, leading to malignancies. Thus, the promoter should have sufficiently high activity in dendritic and other cells, but not contain an enhancer. Based on these criteria, viral promoters, such as the CMV promoter, are not ideal because of the presence of strong enhancers. These criteria are summarized as follows:

1. high expression in dendritic cells to induce maximal immune responses;
2. expression in other transduced cell types sufficient for elimination by the induced immune response; and
3. lack of an enhancer element to avoid insertional effects.

The vector should be capable of being generated at high titers to maximize delivery and expression, while minimizing contaminants.

Thus, a need exists in the art for improved vectors. The present invention fulfils these needs in the art.

SUMMARY OF THE INVENTION

The invention encompasses compositions comprising lentiviral vectors and methods of making and using the vectors. In one embodiment, the invention encompasses a lentiviral vector comprising an MHC class I, MHC class II, or β2 microglobulin upstream promoter sequence, preferably further comprising an MHC class I or β2 microglobulin promoter.

The invention encompasses methods for producing a lentiviral vector comprising inserting at least 300 nucleotides, preferably 300-400, 300-600 or 300-1100 nucleotides, of an MHC class I, MHC class II, or β2 microglobulin upstream promoter sequence into a lentiviral vector.

Preferably, the upstream promoter sequence is inserted upstream of an MHC class I or β2 microglobulin promoter. Most preferably, the upstream promoter sequence is inserted in the same orientation as the MHC class I or β2 microglobulin promoter.

In some embodiments, the upstream promoter sequence is an MHC class I upstream promoter sequence. In some embodiments, the upstream promoter sequence is a β2 microglobulin upstream promoter sequence, preferably comprising SEQ ID NO:1 or SEQ ID NO:27.

In some embodiments, the promoter is an MHC class I promoter. In some embodiments, the promoter is a β2 microglobulin promoter.

The invention encompasses a lentiviral vector comprising at least 300 nucleotides, preferably 300-400, 300-600 or 300-1100 nucleotides, of an MHC class I, MHC class II, or β2 microglobulin upstream promoter sequence.

Preferably, the upstream promoter sequence is upstream of an MHC class I or β2 microglobulin promoter. Most preferably, the upstream promoter sequence is in the same orientation as the MHC class I or β2 microglobulin promoter.

In some embodiments, the upstream promoter sequence is an MHC class I upstream promoter sequence. In some embodiments, the upstream promoter sequence is a β2 microglobulin upstream promoter sequence, preferably comprising SEQ ID NO:1 or SEQ ID NO:27. In some embodiments, the promoter is an MHC class I promoter. In some embodiments, the promoter is a β2 microglobulin promoter.

Preferably, the MHC class I promoter is an HLA-A2 promoter, HLA-B7 promoter, or an HLA-E promoter.

Preferably, the upstream promoter sequence is an HLA-A2, HLA-B7, or an HLA-E, or HLA-DRα upstream promoter sequence.

Preferably, the lentiviral vector comprises a lentiviral cPPT/CTS sequence. Preferably, the lentiviral vector comprises a lentiviral ψ (psi) sequence.

The invention encompasses an isolated host cell comprising a lentiviral vector of the invention. The invention encompasses a lentiviral vector of the invention for use as a medicament or vaccine, particularly for gene therapy.

In preferred embodiments, the upstream promoter sequence comprises the nucleotide sequence of any one of SEQ ID NO:2, SEQ ID NO:3, SEQ ID NO:4, SEQ ID NO:5, SEQ ID NO:6, SEQ ID NO:7, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

BRIEF DESCRIPTION OF THE DRAWINGS

FIG. 7 depicts the nucleotide sequences of β2-microglobulin (SEQ ID NO:1) and MHC Class I (SEQ ID NOs:2-7) upstream promoter sequences. A consensus sequence is shown (SEQ ID NO:8).

FIG. 8A-B depicts the nucleotide sequences of β2-microglobulin (SEQ ID NO:40), MHC Class I (SEQ ID NOs:37-39), and MHC Class II (SEQ ID NO:41) promoters and short upstream promoter sequences. The locations of the κB, ISRE, and SXY module are indicated.

FIG. 9A-C depicts the nucleotide sequences of β2-microglobulin (SEQ ID NO:45), MHC Class I (SEQ ID NOs:42-44), and MHC Class II (SEQ ID NO:46) promoters and long upstream promoter sequences. The locations of the κB, ISRE, and SXY module are indicated.

DETAILED DESCRIPTION OF THE INVENTION

Figure 1:
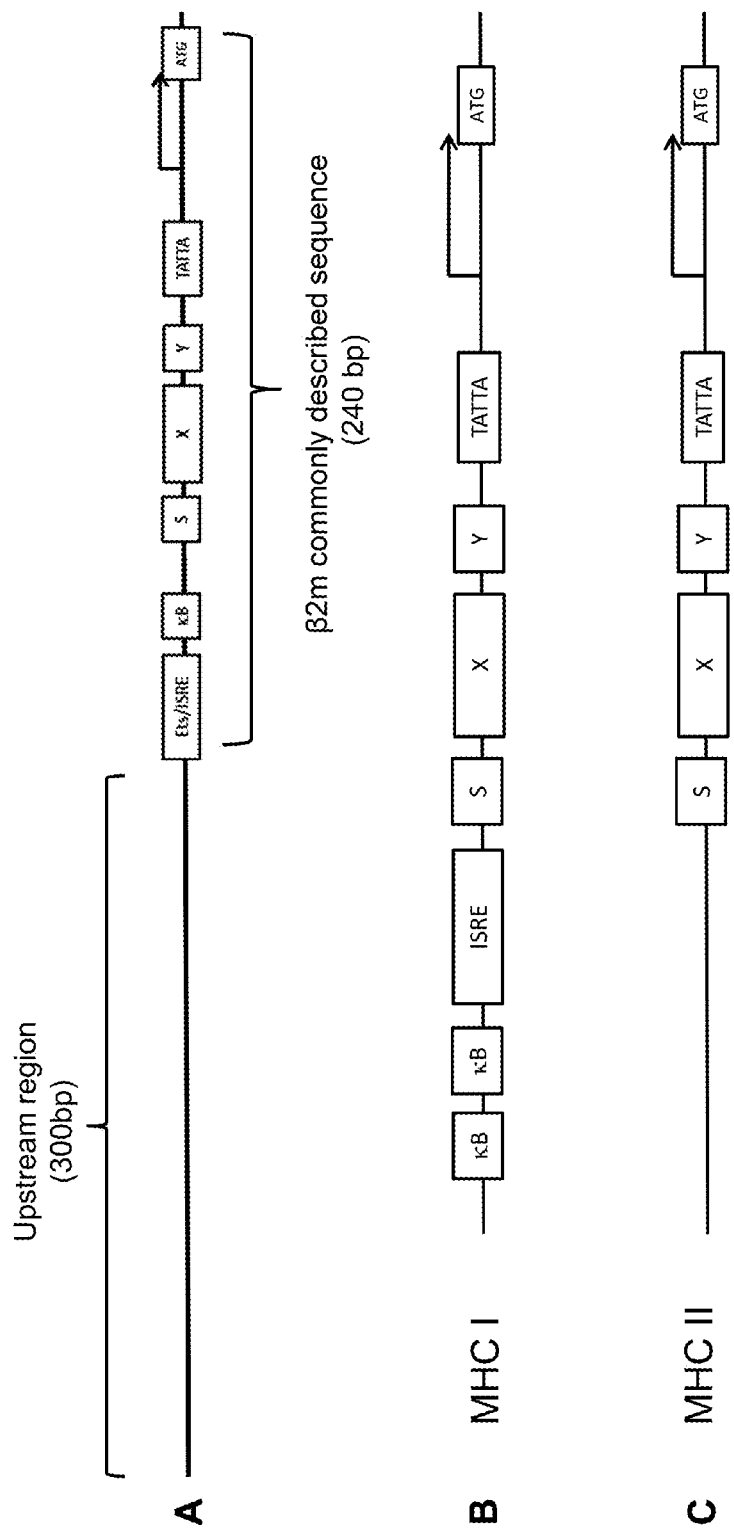
FIGS. 1 A, B, and C depict schematic representations of (A) the β2m promoter (promoter region and upstream chromosomal region), (B) the MHC class I promoter, and (C) the MHC class II promoter.

The effect of MHC class I, MHC class II, or β2 microglobulin upstream promoter sequences on lentiviral vector titers was examined. The upstream promoter sequences are located upstream of the Ets/ISRE and NF-Kb binding sites found in the β2 microglobulin and MHC class I promoters (FIG. 1). The upstream promoter sequences are located upstream of the SXY module found in MHC class II promoters (FIG. 1). The human β2-microglobulin (β2m) promoter shows some similarity to the MHC Class I promoters, but it contains the ISRE upstream of a single NF-Kb binding site.

The upstream promoter sequences of β2m and MHC Class I promoters show some similarity at the nucleotide level (FIG. 7). Two upstream promoter sequences were selected for analysis, β2m and HLA-E.

First, an upstream promoter sequence of β2m was inserted into a lentiviral vector upstream of and in the same orientation as the β2m and MHCI promoters HLA-A2, HLA-B7, and HLA-E. For comparison, the upstream promoter sequence of β2m was inserted into lentiviral vectors upstream of and in the same orientation as the Ubiquitin (UBC) gene promoter, the CMV promoter, or an MHCII promoter (HLA-DRα). In these vectors, the promoters drive expression of green fluorescent protein (GFP).

To look for expression, the vectors were packaged by cotransfection in HEK-293T cells with an encapsidation plasmid and a plasmid providing VSV.G envelope, essentially as described in Naldini et al, 1996, Science 272:263-7. HEK-293T cells were then transduced with particles of the different vectors. Expression was detected in the cells with all vectors.

Figure 2:
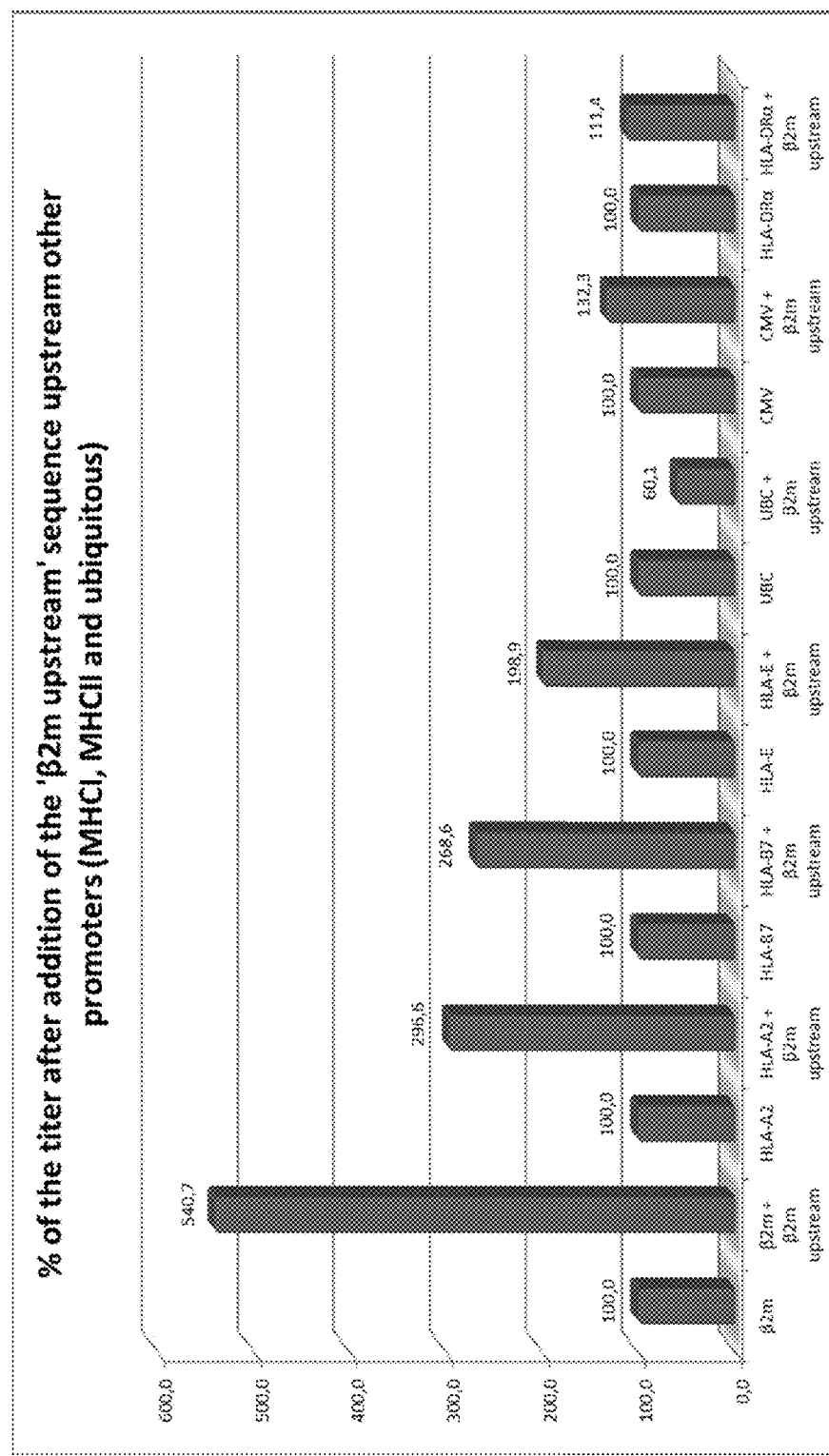
FIG. 2 depicts production yields of various lentiviral constructs, with or without the β2m upstream promoter sequence cloned upstream of various promoters. The β2m upstream promoter sequence was cloned upstream of various promoters by fusion PCR. The resulting lentiviral vectors were produced and used to transduce HEK-293T cells, and the percentage of transduced cells were evaluated by specific qPCR.

The addition of the β2m upstream promoter sequence into lentiviral vectors with a β2m, HLA-A2, HLA-B7, or HLA-E promoter resulted in an approximately 2-5 fold increase in viral titers. In contrast, addition of the β2m upstream promoter sequence into lentiviral vectors with a CMV promoter, an UBC promoter, or an HLA-A2 promoter demonstrated little effect on the titers (FIG. 2). Thus, the β2m upstream promoter sequence could increase titers from a lentiviral vector containing a β2m or MHCI promoter.

Figure 3:
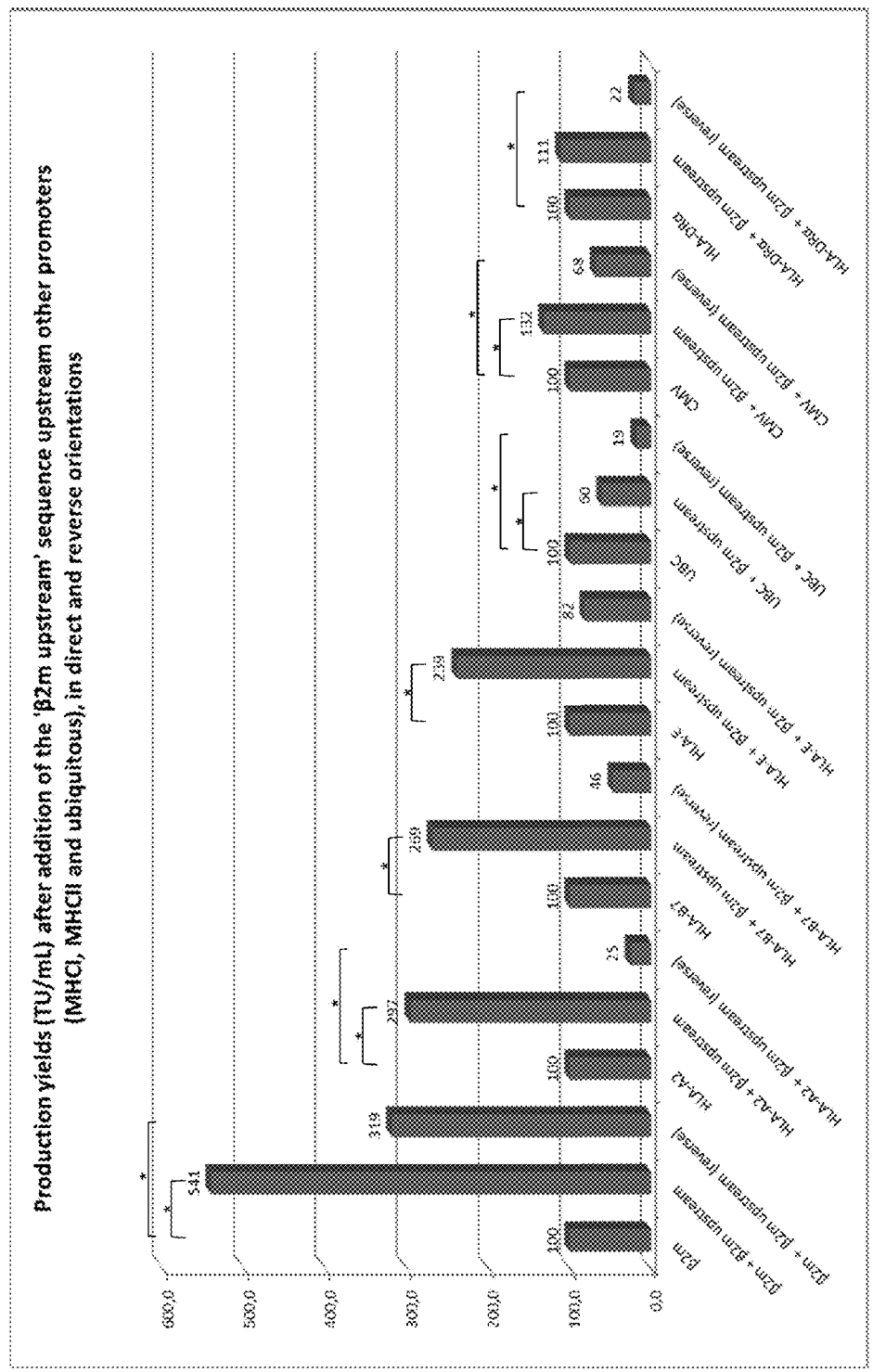
FIG. 3 depicts production yields of various lentiviral constructs, with or without the β2m upstream promoter sequence cloned upstream of various promoters, in direct or reverse orientation. The β2m upstream promoter sequence was cloned upstream of various promoters by fusion PCR, either in direct (5'-3') or reverse (3'-5') orientation. The resulting lentiviral vectors were produced and used to transduce HEK-293T cells, and the percentage of transduced cells were evaluated by specific qPCR.

Next, the upstream promoter sequence of β2m was inserted into a lentiviral vector upstream of and in the reverse orientation as the β2m and MHCI promoters HLA-A2, HLA-B7, and HLA-E. For comparison, the upstream promoter sequence of β2m was inserted into lentiviral vectors upstream of and in the reverse orientation as the Ubiquitin (UBC) genes promoter, the CMV promoter, or an MHCII promoter (HLA-DRα). The addition of the β2m upstream promoter sequence into lentiviral vectors upstream of and in the reverse orientation as the HLA-A2, HLA-B7, or HLA-E promoter did not result in an increase in viral titers (FIG. 3). In fact, several of the lentiviral vectors with the upstream promoter sequence of β2m inserted in the reverse orientation showed a decrease in titers. Thus, the increase in titers from a lentiviral vector caused by the β2m upstream promoter sequence was orientation dependent.

Figure 4:
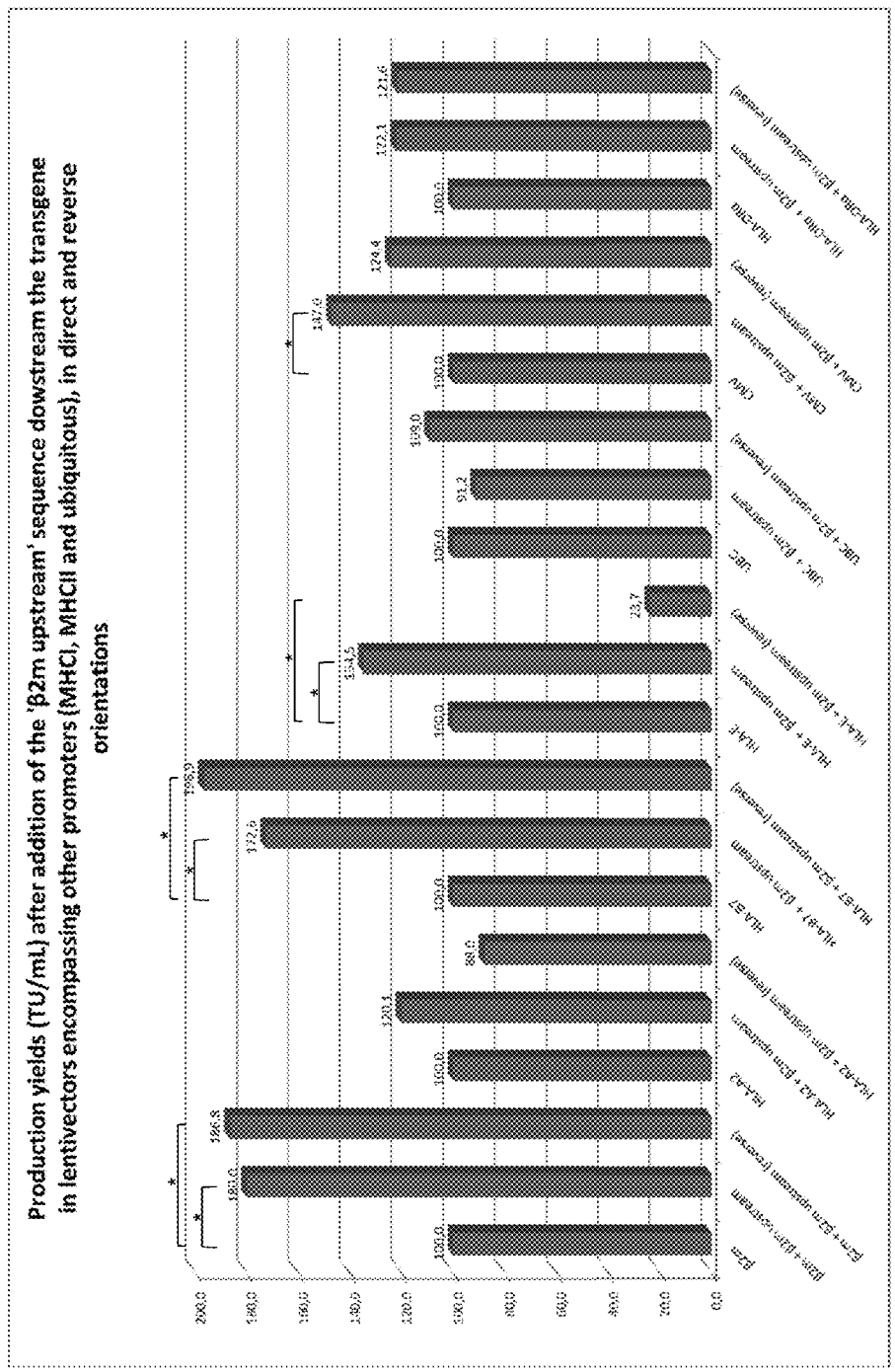
FIG. 4 depicts production yields of various lentiviral constructs, with or without the β2m upstream promoter sequence cloned downstream of the transgene (GFP), in direct or reverse orientation. The β2m upstream promoter sequence was cloned downstream of the transgene (GFP) of lentiviral constructs harboring various promoters, either in direct (5'-3') or reverse (3'-5') orientation. The resulting lentiviral vectors were produced and used to transduce HEK-293T cells, and the percentage of transduced cells were evaluated by specific qPCR.

Next, the upstream promoter sequence of β2m was inserted into a lentiviral vector downstream of the transgene and in the same or reverse orientation as the β2m and MHCI promoters HLA-A2, HLA-B7, and HLA-E. For comparison, the upstream promoter sequence of β2m was inserted into lentiviral vectors downstream of the transgene and in the same or reverse orientation as the Ubiquitin (UBC) genes promoter, the CMV promoter, or an MHCII promoter (HLA-DRα). The addition of the β2m upstream promoter sequence downstream of the transgene and in the same orientation as the β2m, HLA-A2, HLA-B7, or HLA-E promoter resulted in only a small increase in viral titers (FIG. 4). Thus, the increase in titers from a lentiviral vector caused by the β2m upstream promoter sequence was position dependent.

Figure 5:
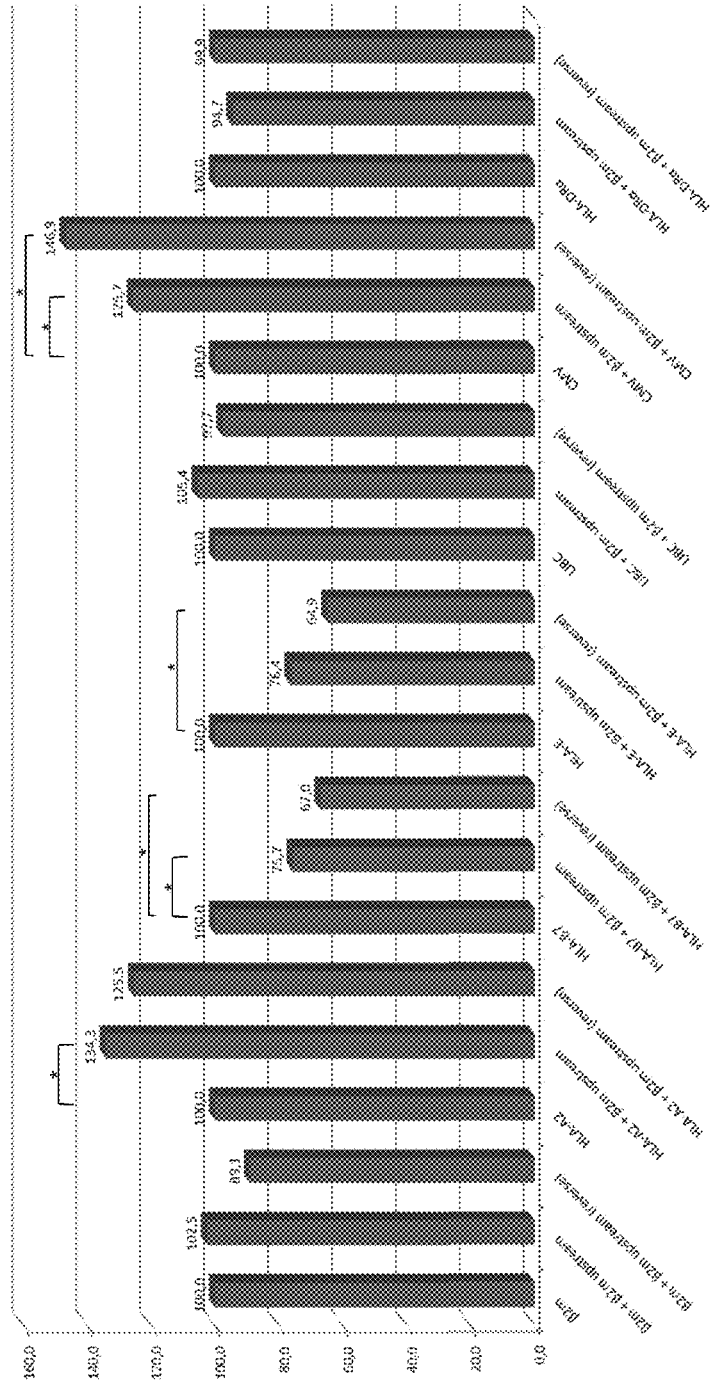
FIG. 5 depicts production yields of various lentiviral constructs, with or without the β2m upstream promoter sequence cloned outside of the proviral sequence (into the plasmidic backbone), in direct or reverse orientation. The β2m upstream promoter sequence was cloned outside the proviral sequence (inside the plasmid backbone) of constructs harboring various promoters, either in direct (5'-3') or reverse (3'-5') orientation. The resulting lentiviral vectors were produced and used to transduce HEK-293T cells, and the percentage of transduced cells were evaluated by specific qPCR.

Next, the upstream promoter sequence of β2m was inserted into a lentiviral vector outside of the LTR-LTR region in the same or reverse orientation as the β2m and MHCI promoters HLA-A2, HLA-B7, and HLA-E. For comparison, the upstream promoter sequence of β2m was inserted into lentiviral vectors outside of the LTR-LTR region in the same or reverse orientation as the Ubiquitin (UBC) genes promoter, the CMV promoter, or an MHCII promoter (HLA-DRα). The addition of the β2m upstream promoter sequence outside of the LTR-LTR region in the same or reverse orientation resulted in no apparent difference in viral titers (FIG. 5). Thus, the increase in titers from a lentiviral vector caused by the β2m upstream promoter sequence was dependent on its presence between the LTRs in the vector.

Next, an upstream promoter sequence of HLA-E was inserted into a lentiviral vector upstream of and in the same or reverse orientation as the β2m and MHCI promoters HLA-A2, HLA-B7, and HLA-E. For comparison, the upstream promoter sequence of HLA-E was inserted into lentiviral vectors upstream of and in the same or reverse orientation as the Ubiquitin (UBC) genes promoter, the CMV promoter, or an MHCII promoter (HLA-DRα).

Figure 6:
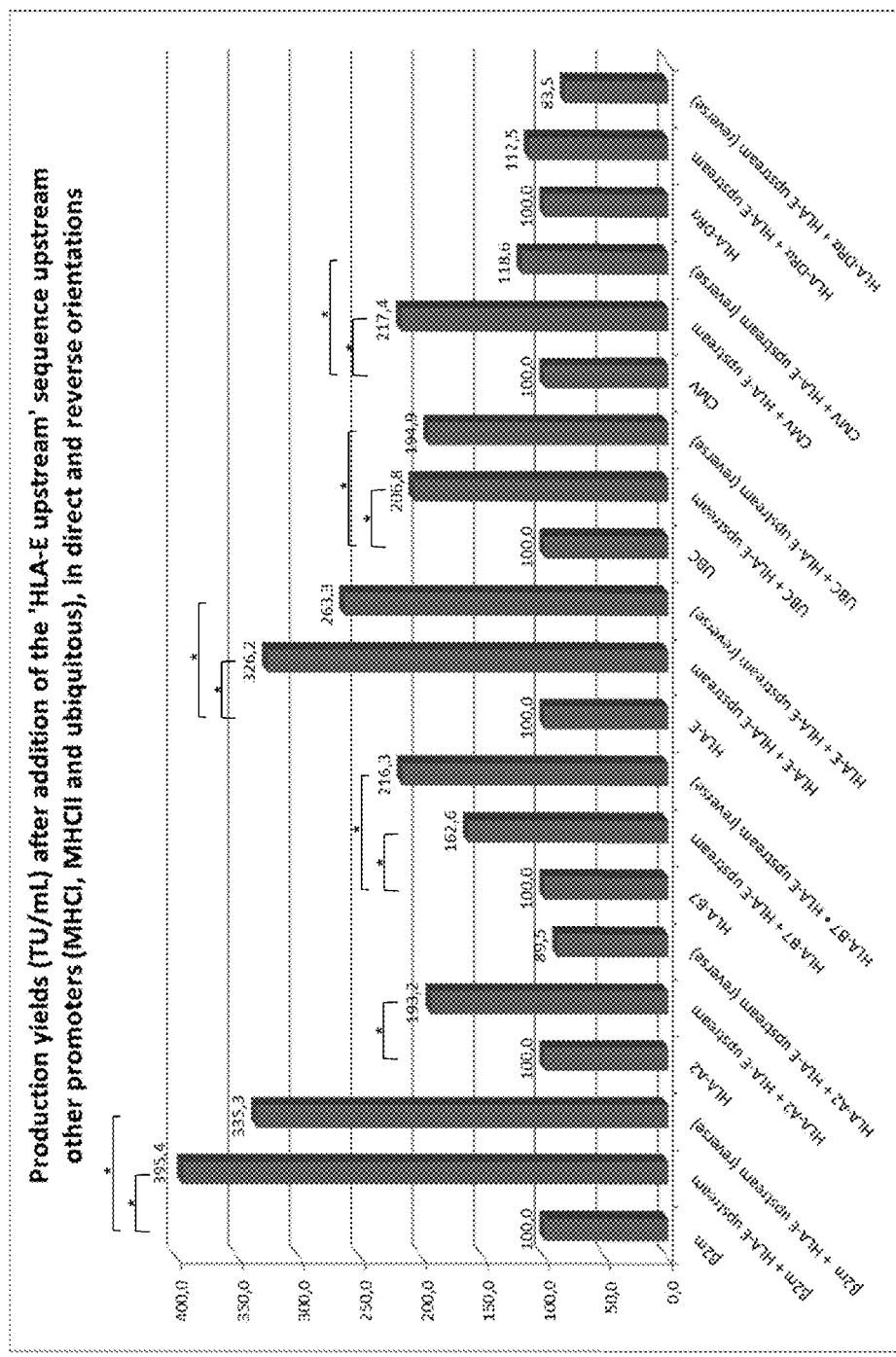
FIG. 6 depicts production yields of various lentiviral constructs, with or without the HLA-E upstream promoter sequence cloned upstream of various promoters, in direct or reverse orientation. The HLA-E upstream promoter sequence was cloned upstream of various promoters by fusion PCR, either in direct (5'-3') or reverse (3'-5') orientation. The resulting lentiviral vectors were produced and used to transduce HEK-293T cells, and the percentage of transduced cells were evaluated by FACS analysis.
Figure 9C:
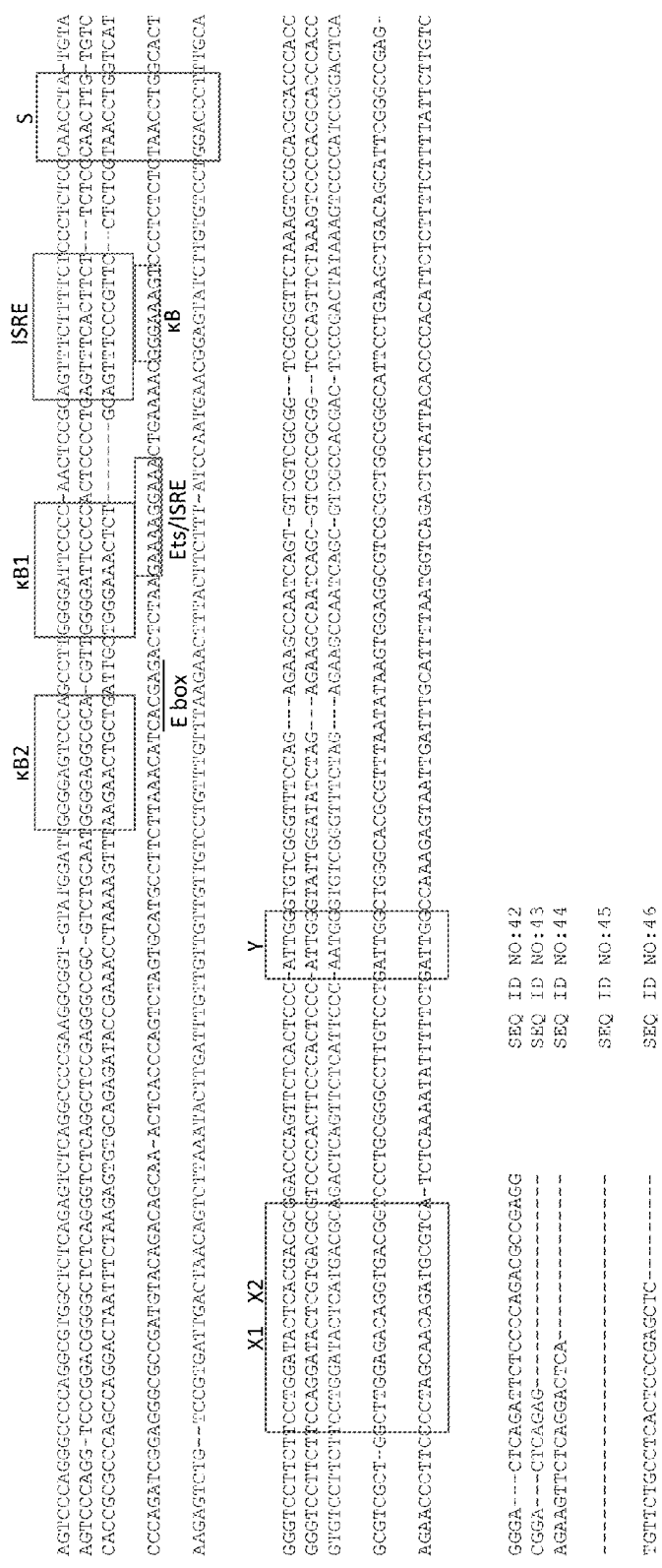

The addition of the HLA-E upstream promoter sequence into lentiviral vectors upstream of the β2m, HLA-A2, HLA-B7, or HLA-E promoter resulted in an approximately 2-4 fold increase in viral titers (FIG. 6). In most constructs, the HLA-E upstream promoter sequence worked similarly in both orientations. The addition of the HLA-E upstream promoter sequence into lentiviral vectors with a CMV promoter or a UBC promoter demonstrated an approximately 2 fold increase in the titers (FIG. 6). However, the addition of the HLA-E upstream promoter sequence into a lentiviral vector with an HLA-DRα promoter demonstrated little or no effect on the titers. Thus, the HLA-E upstream promoter sequence could increase titers from a lentiviral vector containing a β2m, MHCI, CMV, or UBC promoter.

An upstream promoter sequence of HLA-A2 was inserted into a lentiviral vector upstream of and in the same or reverse orientation as the β2m promoter. The addition of the HLA-A2 upstream promoter sequence into lentiviral vectors upstream of the β2m promoter resulted in an approximately 3-4 fold increase in viral titers in both orientations.

An upstream promoter sequence of HLA-B7 was inserted into a lentiviral vector upstream of and in the same or reverse orientation as the β2m promoter. The addition of the HLA-B7 upstream promoter sequence into lentiviral vectors upstream of the β2m promoter resulted in an approximately 10 fold increase in viral titers in the same orientation and an approximately 4 fold increase in viral titers in the reverse orientation.

An upstream promoter sequence of HLA-DRα was inserted into a lentiviral vector upstream of and in the same or reverse orientation as the β2m promoter. The addition of the HLA-DRα upstream promoter sequence into lentiviral vectors upstream of the β2m promoter resulted in an approximately 6 fold increase in viral titers in the same orientation and an approximately 4 fold increase in viral titers in the reverse orientation.

Figure 10:
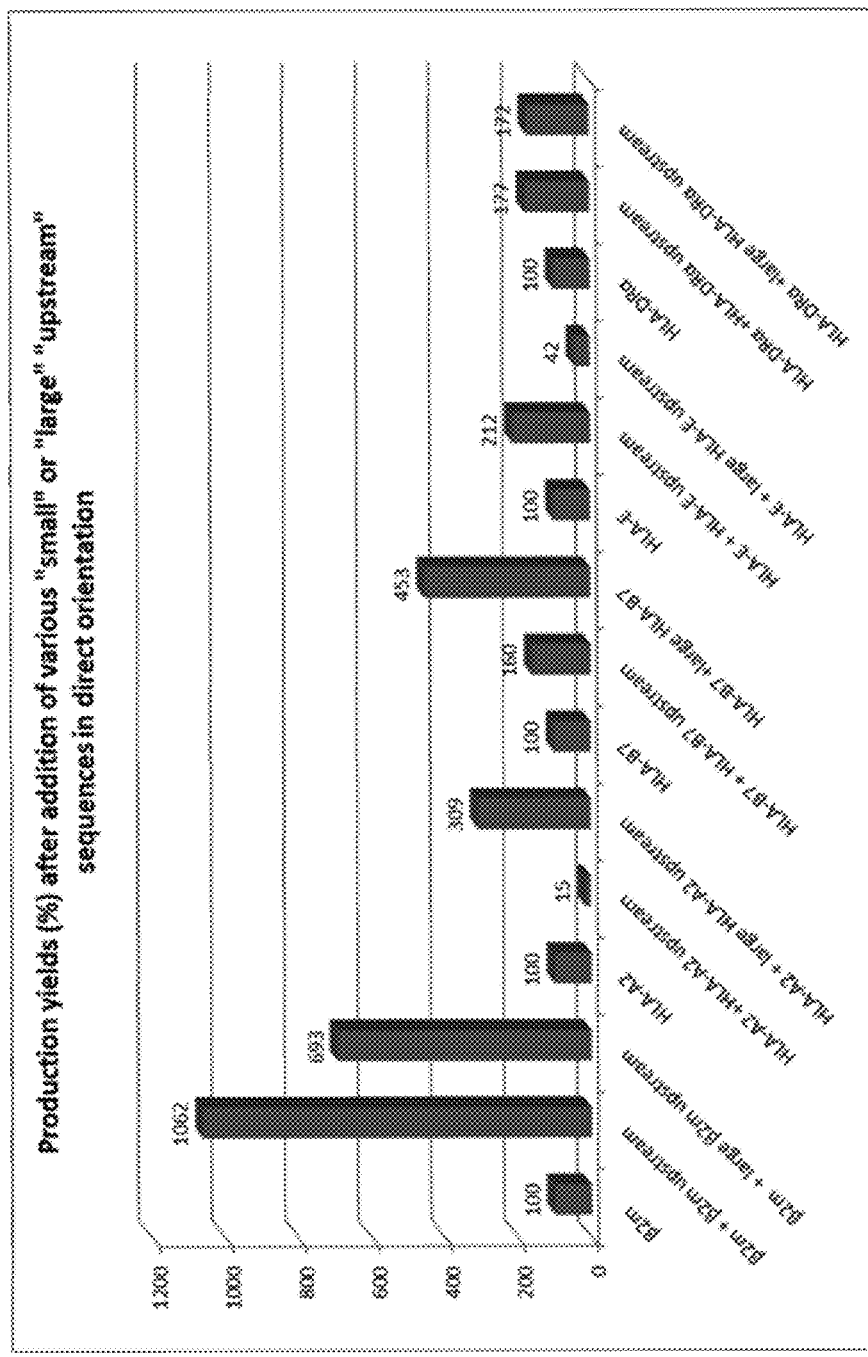
FIG. 10 depicts production yields of various lentiviral constructs, with short or long β2-m, HLA-A2, HLA-B7, HLA-E, or HLA-DRα upstream promoter sequences upstream of their natural promoters, in direct orientation.

Since the upstream sequences were all of about 300-400 nt in size, the effect of larger upstream sequences (500-1100 nt) was investigated. A larger upstream promoter sequence of β2m (1058 bp) was inserted into a lentiviral vector upstream of and in the same orientation as the β2m promoter. The larger upstream promoter sequence did not further increase viral titers, but did retain most of the increased viral titers, as compared to the smaller (330 bp) upstream sequence (FIG. 10).

A larger upstream promoter sequence of HLA-A2 (531 bp) was inserted into a lentiviral vector upstream of and in the same orientation as the HLA-A2 promoter. In this case, the larger HLA-A2 upstream promoter sequence increased viral titers 3 fold; whereas, the smaller (322 bp) HLA-A2 upstream sequence had a negative effect on the HLA-A2 promoter (FIG. 10).

A larger upstream promoter sequence of HLA-B7 (511 bp) was inserted into a lentiviral vector upstream of and in the same orientation as the HLA-B7 promoter. In this case, the larger HLA-B7 upstream promoter sequence further increased viral titers 2-3 fold as compared to the smaller (352 bp) HLA-B7 upstream sequence (FIG. 10). A larger upstream promoter sequence of HLA-E (1047 bp) was inserted into a lentiviral vector upstream of and in the same orientation as the HLA-E promoter. The larger upstream promoter sequence eliminated the increase in viral titers, as compared to the smaller (328 bp) upstream sequence (FIG. 10).

A larger upstream promoter sequence of HLA-DRα (522 bp) was inserted into a lentiviral vector upstream of and in the same orientation as the HLA-DRα promoter. In this case, the larger HLA-DRα upstream promoter sequence had the same effect on the viral titers as compared to the smaller (356 bp) HLA-DRα upstream sequence (FIG. 10).

The effect of the insertion of multiple upstream promoter sequences was investigated. The HLA-E upstream promoter sequence was inserted into a lentiviral vector upstream, downstream, and both upstream and downstream of the β2m promoter. While insertion upstream resulted in a 3-4 fold increase in titers, insertion downstream had no effect on titers and insertion both upstream and downstream resulted in decrease in viral titers.

The present invention has thus, as a main object, a lentiviral vector comprising a β2m or MHCI or MHCII upstream promoter sequence, and methods for making and using such a vector.

Lentiviral Vector

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector contains cis-acting packaging sequences, but lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a lentiviral particle vector, such as an RNA molecule(s) within a complex of lentiviral and other proteins. Typically, lentiviral particle vectors, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA "flap", which acts as a signal for uncoating of the pre-integration complex at the nuclear pore and efficient importation of the expression cassette into the nucleus of non-dividing cells, such as dendritic cells.

In one embodiment, the invention encompasses a lentiviral vector comprising a central polypurine tract and central termination sequence referred to as cPPT/CTS sequence as described, in particular, in the European patent application EP 2 169 073.

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J Virol.* 72(10):8150-7; Zufferey et al., 1998, *J Virol* 72(12):9873-80).

In one embodiment, the invention encompasses a lentiviral vector comprising LTR sequences, preferably with a mutated U3 region (ΔU3) removing promoter and enhancer sequences in the 3' LTR.

The packaging sequence ψ (psi) is incorporated to support encapsidation of the polynucleotide sequence into the vector particles (Kessler et al., 2007, *Leukemia*, 21(9):1859-74; Paschen et al., 2004, *Cancer Immunol Immunother* 12(6): 196-203).

In one embodiment, the invention encompasses a lentiviral vector comprising a lentiviral packaging sequence ψ (psi) and an MHC class I, MHC Class II, or β2 microglobulin upstream promoter sequence.

Further additional functional sequences, such as a transport RNA-binding site or primer binding site (PBS) or a Woodchuck PostRegulation Element (WPRE), can also be advantageously included in the lentiviral vector polynucleotide sequence of the present invention, to obtain a more stable expression of the transgene in vivo.

In one embodiment, the invention encompasses a lentiviral vector comprising a PBS. In one embodiment, the invention encompasses a lentiviral vector comprising a WPRE and/or an IRES.

Thus, in a preferred embodiment, the lentiviral vector comprises an MHC class I, MHC Class II, or β2 microglobulin upstream promoter sequence, at least one cPPT/CTS sequence, one ψ sequence, one (preferably 2) LTR sequence, and an expression cassette including a transgene under the transcriptional control of a promoter, particularly an MHC class I or β2 microglobulin promoter.

Transgene

The invention encompasses a lentiviral vector containing a transgene. Within the context of this invention, a "transgene" is a nucleic acid sequence within a lentiviral vector that is not normally present in a cell to be transduced with the lentiviral vector. The lentiviral vector serves to introduce this sequence into the transduced cell. The term "transgene" does not include those sequences of the vector that facilitate transduction of the transgene. The transgene may be a nucleic acid sequence from another organism. Alternatively, the transgene may be a nucleic acid sequence from the same organism, but having different regulatory sequences controlling its expression. The transgene may be a sense or antisense nucleic acid molecule. According to a preferred embodiment of the invention, the transgene sequence encodes an immunogenic polypeptide.

Preferably, the immunogenic polypeptide is viral, parasitic, bacterial, or fungal. In one embodiment, the immunogenic polypeptide is a tumor antigen.

This immunogenic polypeptide preferably comprises one or several epitope(s) from agents of infectious diseases, for example antigen(s) from Gag, Pol, and/or Nef proteins of HIV.

Several epitopes forming a polyepitope may also be encoded by the transgene of the invention.

In a particular embodiment, such epitope is derived from target antigens identified in tumors, and can be chosen in such a way that a cell-mediated immune response is obtained against it. Target antigens are well documented in the art, which can be selected with respect to several types of tumors and in particular in melanomas or in carcinomas, including renal carcinomas, bladder carcinomas, colon carcinomas, lung carcinomas, breast cancers, leukemias, and lymphomas.

B2M and MHCI Promoters

The invention encompasses the insertion of a β2m or MHC Class I (MHCI) promoter into a lentiviral vector. As used herein, an "MHC Class I (MHCI) promoter" includes a naturally occurring or synthetic MHC Class I promoter. The term "MHC Class I promoter" does not include a β2m promoter.

Naturally Occurring MHCI and a β2m Promoters

Examples of naturally occurring MHCI promoters are the HLA-A2, HLA-B7, HLA-Cw5, HLA-E, HLA-G gene promoters. These naturally occurring MHCI promoters are generally cloned or reproduced from the promoter region of a gene encoding the MHC class I protein, or referred to as putatively encoding such proteins in genome databases (ex: NCBI polynucleotide database http://www.ncbi.nlm.nih.gov/guide/dna-rna). Both β2m and class I MHC proteins enter the Major Histocompatibility Complex (MHC). Preferred promoters are set forth in U.S. Patent Publn. 2014/0120132-A1, which are hereby incorporated by reference.

The proteins encoded by these genes are found in almost all cell types. MHCI proteins are generally present at the surface of the membrane of leucocytes, where they are associated with the β2-microglobulin (β2m) protein. The role of these associated proteins is to present peptides from endogenous sources to CD8+ T cells. They thus play a central role to the generation of the antigen-specific immune response. Because β2m and MHC proteins have been widely studied and described for many years, their genes are well characterized and detectable using sequence comparison tools, such as the BLAST method (Altschul, S. F. et al. (1990). Basic local alignment search tool. *J. Mol. Biol.* 215(3):403-410).

β2m and MHC class I promoters share the ability to be strongly activated in dendritic cells, as well as, to lower intensity, in the majority of the other human body tissues.

The β2m and MHC class I promoters of the invention can contain further regulatory elements, such as one or more Sp1 and ETs binding sites. In a preferred embodiment, the MHC class I promoter contains 2 Sp1 binding sites and 1 Ets binding site. In other embodiments, Ap1 and/or Ap2 sites are further contained in the MHC class I promoter.

Preferred MHC class I promoters are human HLA-A2, HLA-B7, HLA-Cw5, HLA-E, HLA-F, and HLA-G promoters.

Synthetic β2m and MHC Class I Promoters

β2m and MHC class I promoters can also be synthetic. Synthetic β2m and MHC class I promoters include promoters that are synthesized using molecular biological techniques to assemble the individual components of an β2m and MHC class I promoter or that are derived from naturally occurring β2m and MHC class I promoters using molecular biological techniques.

ISRE

The transcription of β2m and MHC class genes is usually mediated by two major regulatory elements: Interferon stimulated response element (ISRE) and the SXY module (encompassing the W/S, X1X2/Site α and Y/enhancer B regulatory elements) (see FIG. 1). See also Van den Elsen, Immunogenetics (1998) 48:208-211.

These regulatory promoter elements are localized in a region extending approximately from nucleotides −220 to −95 upstream of the transcription initiation site. They mediate tissue-specific and cytokine-induced transcription of β2m and MHC class I genes.

The ISRE of β2m and MHC class I gene promoters generally contains binding sites for interferon regulatory factor (IRF) family members. It is thus a property of MHC class I promoters to bind to interferon regulatory factor (IRF) family members. This may be verified, for example, by gel shift assays.

NF-κB Binding Site

Another regulatory element, the enhancer A (containing binding sites for nuclear transcription factor κB (NF-κB)) is present in most cases. It is thus a property of β2m and MHC class I promoters to bind to nuclear transcription factor κB (NF-κB). This may be verified, for example, by gel shift assays.

SXY Module

In addition to ISRE, β2m and MHC class I promoters generally share another set of conserved upstream sequence motifs, consisting of four regulatory elements: the S or W box, the X1/CREX2 boxes or site α, and the Y box or enhancer B, which together are termed the SXY module. This SXY module is generally cooperatively bound by a multiprotein complex containing regulatory factor X (RFX; consisting of RFX5, RFXB/ANK and RFXAP), cAMP response element binding protein (CREB)/activating transcription factor (ATF), and nuclear factor Y (NFY), which acts as an enhanceosome driving transactivation of these genes. It is thus a property of β2m and MHC class I promoters to bind to these factors. This may be verified, for example, by gel shift assays.

In contrast, MHC class II promoters do not display enhancer A, nor ISRE, elements (Van den Elsen, P. J. et al, 1998, *Immunogenetics.* 48:208-221). Furthermore, RFX and CIITA in MHC class II gene regulation have been found of crucial importance as illustrated by studies with cell lines established from patients with the bare lymphocyte syndrome (BLS), a severe combined immunodeficiency due to mutations in one of the RFX subunits or CIITA (DeSandro, A. et al., 1999, *Am J Hum Genet*, 65:279-286). Also, lack of either CIITA or one of the RFX subunits affects the functioning and assembly of the MHC enhanceosome, respectively, leading to a lack of MHC class II and reduced levels of MHC class I transcription (Van den Elsen, P. J. et al. 2004, *Current Opinion in Immunology*, 16:67-75).

β2M and MHCI and MHCII Upstream Promoter Sequences

The invention encompasses the insertion of a β2m, MHC Class I (MHCI), or MHC Class II (MHCII) upstream promoter sequence into a lentiviral vector. As used herein, a "β2m upstream promoter sequence" refers to 1100 base pairs or less of the sequences found immediately upstream of the Ets/ISRE binding site in the naturally occurring β2 microglobulin promoter, as illustrated in FIGS. 8A-B and FIG. 9A-C. See also, FIG. 1 of Van den Elsen et al., Current Opinion in Immunology 2004, 16:67-75, which is hereby incorporated by reference. As used herein, a "MHC Class I (MHCI) upstream promoter sequence" refers to 1100 base pairs or less of the sequences found immediately upstream of the NF-Kb binding site in the naturally occurring MHC Class I promoters, as illustrated in FIGS. 8A-B and FIG. 9A-C. Examples of β2m and MHC Class I (MHCI) upstream promoter sequences are shown in FIG. 7. As used herein, a "MHC Class II (MHCII) upstream promoter sequence" refers to 1100 base pairs or less of the sequences found immediately upstream of the SXY module in the naturally occurring MHC class II promoter, as illustrated in FIGS. 8A-B and FIG. 9A-C.

In various embodiments, the upstream promoter sequence comprises less than 1100, 1000, 900, 800, 700, 600, 550, 500, 450, 400, or 350 nucleotides of an MHC class I, MHC class II, or β2 microglobulin upstream promoter sequence In various embodiments, the upstream promoter sequence comprises at least 300, 305, 310, 315, 320, 325, 330, 335, 350, 357, 400, 450, 500, 600, 700, 800, 900, or 1000 nucleotides of an MHC class I, MHC class II, or β2 microglobulin upstream promoter sequence.

In various embodiments, the upstream promoter sequence comprises 300, 305, 310, 315, 320, 325, 330, 335, 350, 357, 400, 450, or 500 to 305, 310, 315, 320, 325, 330, 335, 350, 357, 400, 450, 550, 600, 700, 800, 900, 1000, or 1100 nucleotides (in all possible combinations of ranges) of an MHC class I, MHC class II, or β2 microglobulin upstream promoter sequence. Preferably, the upstream promoter sequence comprises 300-400, 300-500, 300-600, 300-700, or 300-1100 nucleotides of an MHC class I, MHC class II, or β2 microglobulin upstream promoter sequence. Most preferably, the upstream promoter sequence comprises 300-335 nucleotides of an MHC class I, MHC class II, or β2 microglobulin upstream promoter sequence.

Preferably, the B2M upstream promoter sequence comprises the nucleotide sequence:
AGAAGTTCTCCTTCTGCTAGGTAGCAT-TCAAAGATCTTAATCTTCTGGGTT TCCGTTTTCTC-GAATGAAAAATGCAGGTCCGAGCAGTTAACTG-GCGGGGGCACC ATTAGCAAGTCACTTAGCATCTCTGGGGCCAGTCT-GCAAAGCGAGGGGGCAGC CTTAATGTGCCTCCA-GCCTGAAGTCCTAGAATGAGCGCCCGGTGTC-CCAAGCTG GGGCGCGCACCCCAGATCGGAGGGCGCCGATGTA-CAGACAGCAAACTCACCC AGTCTAGTGCATGCCT-TCTTAAACATCACGAGACTC (SEQ ID NO:1). Preferably, the B2M upstream promoter sequence comprises the nucleotide sequence SEQ ID NO:27 or 28.

Preferably, the MHC Class I upstream promoter sequence comprises an HLA-A2, HLA-B7, HLA-Cw5, HLA-E, or HLA-G upstream promoter sequence.

Preferably, the MHC Class I upstream promoter sequence comprises the nucleotide sequence of any of SEQ ID NOs: 2-7 or SEQ ID NO:29-34.

Preferably, the MHC Class I upstream promoter sequence comprises the nucleotide sequence:

```
                                        (SEQ ID NO: 2)
CTGGAGGGCAATGGCACGATCTTGGCTCACCGCAACCTCCTCCTCCTGG

GTTCAAGTGATTCTCCTGCCTCAGCCTCCCAAGTAGCCAGGATTACAGC

CATGCGCCACCACGCCGGCTAATTTTTTGGACTTTTAGTAGAGACAGGG

TTTCTCCATATTGGTCGGGCTGGTCTCGAACTCCCAACCTCAGGTGATC

AGCCCGCCTTGGCCTCCCAAAGTGCTGAGATTACAGGCGTGAGCCACCG

CGCCCAGCCAGGACTAATTTCTAAGAGTGTGCAGAGATACCGAAACCTA

AAAGTT.
```

Preferred upstream promoter sequences include the following:

Upstream β2m (330 bp):
```
                                        (SEQ ID NO: 27)
GAGAAACCCTGCAGGGAATTCCCCAGCTGTAGTTATAAACAGAAGTTCTC

CTTCTGCTAGGTAGCATTCAAAGATCTTAATCTTCTGGGTTTCCGTTTTC

TCGAATGAAAAATGCAGGTCCGAGCAGTTAACTGGCGGGGGCACCATTAG

CAAGTCACTTAGCATCTCTGGGGCCAGTCTGCAAAGCGAGGGGGCAGCCT

TAATGTGCCTCCAGCCTGAAGTCCTAGAATGAGCGCCCGGTGTCCCAAGC

TGGGGCGCGCACCCCAGATCGGAGGGCGCCGATGTACAGACAGCAAACTC

ACCCAGTCTAGTGCATGCCTTCTTAAACAT
```

Upstream β2m (1058 bp):
```
                                        (SEQ ID NO: 28)
CTTCCAAGATCTCTGCCCCTCCCCATCGCCATGGTCCACTTCCTCTTCTC

ACTGTTCCTCTTAGAAAAGATCTGTGGACTCCACCACCACGAAATGGCGG

CACCTTATTTATGGTCACTTTAGAGGGTAGGTTTTCTTAATGGGTCTGCC

TGTCATGTTTAACGTCCTTGGCTGGGTCCAAGGCAGATGCAGTCCAAACT

CTCACTAAAATTGCCGAGCCCTTTGTCTTCCAGTGTCTAAAATATTAATG

TCAATGGAATCAGGCCAGAGTTTGAATTCTAGTCTCTTAGCCTTTGTTTC

CCCTGTCCATAAAATGAATGGGGGTAATTCTTTCCTCCTACAGTTTATTT

ATATATTCACTAATTCATTCATTCATCCATCCATTCGTTCATTCGGTTTA

CTGAGTACCTACTATGTGCCAGCCCCTGTTCTAGGGTGGAAACTAAGAGA

ATGATGTACCTAGAGGGCGCTGGAAGCTCTAAAGCCCTAGCAGTTACTGC

TTTTACTATTAGTGGTCGTTTTTTTCTCCCCCCCGCCCCCCGACAAATCA

ACAGAACAAAGAAAATTACCTAAACAGCAAGGACATAGGGAGGAACTTCT

TGGCACAGAACTTTCCAAACACTTTTTCCTGAAGGGATACAAGAAGCAAG

AAAGGTACTCTTTCACTAGGACCTTCTCTGAGCTGTCCTCAGGATGCTTT

TGGGACTATTTTTCTTACCCAGAGAATGGAGAAACCCTGCAGGGAATTCC

CAAGCTGTAGTTATAAACAGAAGTTCTCCTTCTGCTAGGTAGCATTCAAA

GATCTTAATCTTCTGGGTTTCCGTTTTCTCGAATGAAAAATGCAGGTCCG

AGCAGTTAACTGGCTGGGGCACCATTAGCAAGTCACTTAGCATCTCTGGG
```

-continued

GCCAGTCTGCAAAGCGAGGGGGCAGCCTTAATGTGCCTCCAGCCTGAAGT

CCTAGAATGAGCGCCCGGTGTCCCAAGCTGGGGCGCGCACCCCAGATCGG

AGGGCGCCGATGTACAGACAGCAAACTCACCCAGTCTAGTGCATGCCTTC

TTAAACAT

Upstream HLA-A2 (322 bp):
(SEQ ID NO: 29)
TACACCTCCATTCCCAGAGCAAGCTTACTCTCTGGCACCAAACTCCATGG

GATGATTTTTCTTCTAGAAGAGTCCAGGTGGACAGGTAAGGAGTGGGAGT

CAGGGAGTCCAGTTCCAGGGACAGAGATTACGGGATAAAAAGTGAAAGGA

GAGGGACGGGGCCCATGCCGAGGGTTTCTCCCTTGTTTCTCAGACAGCTC

TTGGGCCAAGACTCAGGGAGACATTGAGACAGAGCGCTTGGCACAGAAGC

AGAGGGGTCAGGGCGAAGTCCAGGGCCCCAGGCGTTGGCTCTCAGGGTCT

CAGGCCCCGAAGGCGGTGTATG

Upstream HLA-A2 (531 bp):
(SEQ ID NO: 30)
GAGTCCTGTTGTAATGCTTTTGGACACATTTATACATTAAGGGGCCAAAG

TCACATTTTTTACCTATTAGATTCCTGATCATTCAGGGGTTACCAAGATT

CTGCTACCCACTGTAGTTAATAAACAAAGAGCAAATTGGTCTCTATTCTG

TCTCATGCACTCAGGCACAACTTTTCCGGATTAAAAACAAAAACAACAAC

AACAAAAATCTACACCTCCATTCCCAGATCAAGCTTACTCTCTGGCACCA

AACTCCATGGGTGATTTTCTTCTAGAAGAGTCCAGGTGGACAGGTAAG

GAGTGGGAGTCAGGGAGTCCAGTTCAGGGACAGAGATAATGGGATGAAAA

GTGAAAGGAGAGGGACGGGGCCCATGCCGAGGGTTTCTCCCTTGTTTCTC

AGACAGCTCCTGGGCCAAGACTCAGGGAGACATTGAGACAGAGCGCTTCG

CACAGGAGCAGAGGGGTCAGGGCGAAGTCCAGGGCCCCAGGCGTGGCTC

TCAGAGTCTCAGGCCCCGAAGGCGGTGTATG

Upstream HLA-B7 (352 bp):
(SEQ ID NO: 31)
AGGTTTAAAGAGAAAACCCCTGTCTCTACACCTCCATTCCCAGGGCGAGC

TCACTCTCTGGCATCAAGTTCCCCGTGCTCAGTTTCCCTACACAAGAGTC

CAAGAGGAGAGGTAAGGAGTGGGAGGCAGGGAGTCCAGTTCAGGGACAGG

GATTCCAGGACGAGAAGTGAAGGGGAAGGGGCTGGGCGCAGCCTGGGGGT

CTCTCCCTGGTTTCCACAGACAGATCCTTGTCCAGGACTCAGGCAGACAG

TGTGACAAAGAGGCTTGGTGTAGGAGAAGAGGGATCAGGACGAAGTCCCA

GGTCCCGGACGGGGCTCTCAGGGTCTCAGGCTCCGAGGGCCGCGTCTGCA

AT

Upstream HLA-B7 (511 bp)
(SEQ ID NO: 32)
GAGTTTAATTGTAATGCTGTTTTGACACAGGTCTTTTACAAATTGGAATT

CTAATCATTCAGGGATTACCAATATTGTGCTACCTACTGTATTAACAAAC

AAAAAGGAAACTGGTCTCTATGAGAATCCCTATGCGGTGCCTTCAGAGAA

AACTTCACCAGGTTTAAAGAGAAAACCCCTGTCTCTACACCTCCATTCCC

AGGGCGAGCTCACTCTCTGGCATCAAGTTCCCCGTGCTCAGTTTCCCTAC

ACAAGAGTCCAAGAGGAGAGGTAAGGAGTGGGAGGCAGGGAGTCCAGTTC

AGGGACAGGGATTCCAGGACGAGAAGTGAAGGGGAAGGGGCTGGGCGCAG

-continued

CCTGGGGGTCTCTCCCTGGTTTCCACAGACAGATCCTTGTCCAGGACTCA

GGCAGACAGTGTGACAAAGAGGCTTGGTGTAGGAGAAGAGGGATCAGGAC

GAAGTCCCAGGTCCCGGACGGGGCTCTCAGGGTCTCAGGCTCCGAGGGCC

GCGTCTGCAAT

Upstream HLA-E (328 bp):
(SEQ ID NO: 33)
ACTAATTTCTTTTTTCTTGTTGCCCAGGCTGGAGGGCAATGGCACGATCT

TGGCTCACCGCAACCTCCTCCTCCTGGGTTCAAGTGATTCTCCTGCCTCA

GCCTCCCAAGTAGCCAGGATTACAGCCATGCGCCACCACGCCGGCTAATT

TTTTGGACTTTTAGTAGAGACAGGGTTTCTCCATATTGGTCGGGCTGGTC

TCGAACTCCCAACCTCAGGTGATCAGCCCGCCTTGGCCTCCCAAAGTGCT

GAGATTACAGGCGTGAGCCACCGCGCCCAGCCAGGACTAATTTCTAAGAG

TGTGCAGAGATACCGAAACCTAAAAGTT

Upstream HLA-E (1047 bp):
(SEQ ID NO: 34)
TTTTTTCCCCTAGACATCTCACTCTGTCGCCCAGGCTGGAGTGCAGTGG

TGTGATCTCGGCTCACTGCAACCACCACCTCTCGGGTTCAAGCAATTCTC

CTATCTCAGCCTCCAGAGTTGCTGGAATTACAGGCGCGCACCACCACACC

CGGCTAATTTTTGTATTGTTAGTAGAGACAGGGTTTCATCATGTTGGCCA

GGTTAGTCTTGAACTCCTGACCTCGTGATCTGCCTGCCTCGGCCTACCAA

AATGCTGCGATTACAGGCGTGAGCCACCGTTCCCGGCCTATACGTTGTTT

ATTTTGGAAAAATTAAAAATTAAGTTTTTTTTCATTAAAGATATGTTATT

TCCGATCAAGAGATCAAGACCATCCTGGCCAACATGGTGAAACCCCGTCT

CTACTAAAAACACAAAAATTAGCTGGGTGTGGTGGCACACGCCTGTAGTT

CCAGTTACTGGGGAGGCTGAGGCAGGAGAATCGCTTGAACCCGGGAGAAG

GAGGTTGCAGTGAGCCGAGATCATGCCACTGCACTCCAGCCTGGGGACAG

AGCAAGACTCTGACTCAAAAAAAAAAAAAAGTTGTTTCTATTAACATGTAA

TGGGTTATTAATATTCTCTTAAATGAATTAATATTTTTAATATTTTGTTT

TAATATCTTTTAATTTATATATGATAAAATTGATACAATCCACAGAAAC

AAAATTTATTTGGGTCCTCACTAATTTCTTTTTTCTTGTTGCCCAGGCTG

GAGGGCAATGGCACGATCTTGGCTCACCGCAACCTCCTCCTCCTGGGTTC

AAGTGATTCTCCTGCCTCAGCCTCCCAAGTAGCCAGGATTACAGCCATGC

GCCACCACGCCGGCTAATTTTTTGGACTTTTAGTAGAGACAGGGTTTCTC

CATATTGGTCGGGCTGGTCTCGAACTCCCAACCTCAGGTGATCAGCCCGC

CTTGGCCTCCCAAAGTGCTGAGATTACAGGCGTGAGCCACCGCGCCCAGC

CAGGACTAATTTCTAAGAGTGTGCAGAGATACCGAAACCTAAAAGTT

Upstream HLA-DRα (356 bp):
(SEQ ID NO: 35)
ATACAGCCTTTCATCCTTCTCCAGTGTTGAGAGTGTTGAACCTCAGAGTT

TCTCCTCTCATTTTCTCTAAATGAGATACAATGCCAGCCATCCCAAGCTC

TTGGCCTGAGTTGATCATCTTGAAGTCTAGGACTCCAAGAAGCATGAAAG

AGCTTCTTTAGTGAAGCTATGTCCTCAGTACTGCCAAAATTCAGACAATC

TCCATGGCCTGACAATTTACCTTCTATTTGGGTAATTTATTGTCCCTTAC

-continued
GCAAACTCTCCAACTGTCATTGCACAGACATATGATCTGTATTTAGCTCT

CACTTTAGGTGTTTCCATTGATTCTATTCTCACTAATGTGCTTCAGGTAT

ATCCCT

Upstream HLA-DRα (522 bp):

(SEQ ID NO: 36)
TAGGCTTTGCCCATTATACTCTCTCATATTCATTGACCTGAATCCTCAAA

TGAGGTGTGTCCATTAGTCAACTCCAATCTCTTGTCATATATAAGATGGT

AGAGATGAGAAGAAGGTAGCTCCTTTACAGCCCACTATTTCCACTAACTA

CTACCTGTGTTTCAAGATACAGCCTTTCATCCTTCTCCAGTGTTGAGAGT

GTTGAACCTCAGAGTTTCTCCTCTCATTTTCTCTAAATGAGATACAATGC

CAGCCATCCCAAGCTCTTGGCCTGAGTTGTTCATCTTGAAGTCTAGGACT

CCAAGAAGCATGAAAGAGCTTCTTTAGTGAAGCTATGTCCTCAGTACTGC

CAAAATTCAGACAATCTCCATGGCCTGACAATTTACCTTCTATTTGGGTA

ATTTATTGTCCCTTACGCAAACTCTCCAGCTGTCATGGCACAGACATATG

ATCTGTATTTAGCTCTCACTTTAGGTGTTTCCATTGATTCTATTCTCACT

AATGTGCTTCAGGTATATCCCT

In some embodiments, the vectors comprise any of SEQ ID Nos. 37-46.

Production of Lentiviral Vectors

In one embodiment, the invention encompasses a method comprising inserting an MHC class I, MHC Class II, or β2 microglobulin upstream promoter sequence into a lentiviral vector. The method can further comprise inserting any of the other nucleic acid elements mentioned herein, such as a DNA flap sequence.

The invention encompasses methods for producing a lentiviral vector comprising inserting at least 300, 305, 310, 315, 320, 325, 330, 335, 350, 357, 400, 450, 500, 600, 700, 800, 900, or 1000 nucleotides of an MHC class I, MHC Class II, or β2 microglobulin upstream promoter sequence into a lentiviral vector.

In various embodiments, the upstream promoter sequence comprises less than 1100, 1000, 900, 800, 700, 600, 550, 500, 450, 400, or 350 nucleotides of an MHC class I, MHC class II, or β2 microglobulin upstream promoter sequence.

The invention encompasses methods for producing a lentiviral vector comprising inserting 300, 305, 310, 315, 320, 325, 330, 335, 350, 357, 400, 450, or 500 to 305, 310, 315, 320, 325, 330, 335, 350, 357, 400, 450, 550, 600, 700, 800, 900, 1000, or 1100 nucleotides (in all possible combinations of ranges) of an MHC class I, MHC class II, or β2 microglobulin upstream promoter sequence into a lentiviral vector. Preferably, the upstream promoter sequence comprises 300-400, 300-500, 300-600, 300-700, or 300-1100 nucleotides of an MHC class I, MHC Class II, or β2 microglobulin upstream promoter sequence.

Most preferably, the upstream promoter sequence comprises 300-335 nucleotides of an MHC class I, MHC Class II, or β2 microglobulin upstream promoter sequence.

Preferably, the MHC class I, MHC Class II, or β2 microglobulin upstream promoter sequence is inserted into a lentiviral vector comprising a MHC class I or β2 microglobulin promoter. The upstream promoter sequence can be in the same or reverse orientation as the promoter.

The invention encompasses methods for producing a lentiviral vector comprising inserting at least 300, 305, 310, 315, 320, 325, 330, 335, 350, 357, 400, 450, 500, 600, 700, 800, 900, or 1000 nucleotides of an MHC class I, MHC Class II, or β2 microglobulin upstream promoter sequence and an MHC class I or β2 microglobulin promoter into a lentiviral vector.

In various embodiments, the upstream promoter sequence comprises less than 1100, 1000, 900, 800, 700, 600, 550, 500, 450, 400, or 350 nucleotides of an MHC class I, MHC Class II, or β2 microglobulin upstream promoter sequence.

The invention encompasses methods for producing a lentiviral vector comprising inserting 300, 305, 310, 315, 320, 325, 330, 335, 350, 357, 400, 450, or 500 to 305, 310, 315, 320, 325, 330, 335, 350, 357, 400, 450, 550, 600, 700, 800, 900, 1000, or 1100 nucleotides (in all possible combinations of ranges) of an MHC class I, MHC Class II, or β2 microglobulin upstream promoter sequence and an MHC class I or β2 microglobulin promoter into a lentiviral vector. Preferably, the upstream promoter sequence comprises 300-400, 300-500, 300-600, 300-700, or 300-1100 nucleotides of an MHC class I, MHC Class II, or β2 microglobulin upstream promoter sequence. Most preferably, the upstream promoter sequence comprises 300-335 nucleotides of an MHC class I, MHC Class II, or β2 microglobulin upstream promoter sequence.

In one embodiment, the MHC class I, MHC Class II, or β2 microglobulin upstream promoter sequence is inserted into the lentiviral vector prior to insertion of a MHC class I or β2 microglobulin promoter.

In one embodiment, the MHC class I, MHC Class II, or β2 microglobulin upstream promoter sequence is inserted into the lentiviral vector after insertion of a MHC class I or β2 microglobulin promoter.

In one embodiment, the MHC class I, MHC Class II, or β2 microglobulin upstream promoter sequence and an MHC class I or β2 microglobulin promoter are inserted together into the lentiviral vector.

In one embodiment, a β2 microglobulin upstream promoter sequence is inserted upstream in the same orientation as an MHC class I or β2 microglobulin promoter.

In one embodiment, an MHC class I or MHC Class II upstream promoter sequence is inserted upstream in the same orientation as an MHC class I or β2 microglobulin promoter.

Preferably, the upstream promoter sequence comprises an β2 microglobulin, HLA-A2, HLA-B7, HLA-Cw5, HLA-E, or HLA-G upstream promoter sequence and the promoter is a β2 microglobulin, HLA-A2, HLA-B7, HLA-Cw5, HLA-E, or HLA-G promoter. All combinations individually are considered part of the invention.

Preferably the upstream promoter sequence comprises a nucleotide sequence comprising any of SEQ ID NO:1-SEQ ID NO:7 or SEQ ID NO:27-SEQ ID NO:36.

Production of Lentiviral Particle Vector

The present invention provides a method for producing a lentiviral particle vector, which contains an MHC class I, MHC Class II, or β2 microglobulin upstream promoter sequence. Thus, the invention encompasses a lentiviral particle vector comprising an MHC class I, MHC Class II, or β2 microglobulin upstream promoter sequence. A lentiviral particle vector (or lentiviral vector particle) comprises a lentiviral vector in association with viral proteins.

The insertion of an MHC class I, MHC Class II, or β2 microglobulin upstream promoter sequence can increase the titer of the vector.

According to one embodiment of this method, the particle vector is obtained in a host cell transformed with a DNA plasmid.

Such a DNA plasmid can comprise:
 bacterial origin of replication (ex: pUC ori);
 antibiotic resistance gene (ex: KanR) for selection; and
more particularly:
 a lentiviral vector comprising an MHC class I, MHC Class II, or β2 microglobulin upstream promoter sequence.

The invention allows the production of recombinant vector particles, comprising the following steps of:
 i) transfecting or transducing a suitable host cell with a lentiviral vector;
 ii) transfecting or transducing said host cell with a packaging plasmid vector, containing viral DNA sequences encoding at least structural and integrase proteins of a retrovirus (preferably lentivirus); Such packaging plasmids are described in the art (Dull et al., 1998, *J Virol*, 72(11): 8463-71; Zufferey et al., 1998, *J Virol* 72(12):9873-80).
 iii) culturing said transfected host cell in order to obtain expression and packaging of said lentiviral vector into lentiviral vector particles; and
 iv) harvesting the lentiviral vector particles resulting from the expression and packaging of step iii) in said cultured host cells.

The host cell transfected or transduced with a packaging plasmid may be a stable packaging cell line. Thus, the method can comprise:
 i) transfecting or transducing a packaging cell line with a lentiviral vector;
 ii) culturing the cell line in order to obtain expression and packaging of said lentiviral vector into lentiviral vector particles; and
 iii) harvesting the lentiviral vector particles resulting from the expression and packaging of step ii) in the cultured cell line.

For different reasons, it may be helpful to pseudotype the obtained retroviral particles, i.e. to add or replace specific particle envelope proteins. For instance, this may be advantageous to have different envelope proteins in order to distinguish the recombinant particle from natural particles or from other recombinant particles. In matter of vaccination strategy, pseudotyped particle vectors are more likely to escape the immune system, when a patient has already developed immunity against lentiviruses. This is particularly helpful when successive injections of similar particle vectors are required for immunizing a patient against a disease.

In order to pseudotype the retroviral particles of the invention, the host cell can be further transfected with one or several envelope DNA plasmid(s) encoding viral envelope protein(s), preferably a VSV-G envelope protein.

An appropriate host cell is preferably a human cultured cell line as, for example, a HEK cell line.

The method for producing the vector particle is carried out in a host cell, which genome has been stably transformed with one or more of the following components: a lentiviral vector DNA sequence, the packaging genes, and the envelope gene. Such a DNA sequence may be regarded as being similar to a proviral vector according to the invention, comprising an additional promoter to allow the transcription of the vector sequence and improve the particle production rate.

In a preferred embodiment, the host cell is further modified to be able to produce viral particle in a culture medium in a continuous manner, without the entire cells swelling or dying. One may refer to Strang et al., 2005, *J Virol* 79(3): 1165-71; Relander et al., 2005, *Mol Ther* 11(3):452-9; Stewart et al., 2009, *Gene Ther*, 16(6):805-14; and Stuart et al., 2011, *Hum gene Ther* (in press), with respect to such techniques for producing viral particles.

An object of the present invention consists of a host cell transformed with a lentiviral particle vector.

The lentiviral particle vectors can comprise the following elements, as previously defined:
 cPPT/CTS polynucleotide sequence; and
 a transgene sequence under control of a promoter,
 an MHC class I, MHC Class II, or β2 microglobulin upstream promoter sequence,
 and optionally one of the additional elements described above.

Methods for Expressing a Transgene in a Cell

The present invention encompasses methods for expressing a transgene in a cell, preferably a non-dividing cell. The method comprises transducing a cell with a lentiviral vector or lentiviral particle vector of the invention under conditions that allow the expression of the transgene.

The cells are preferably mammalian cells, particularly human cells. Particularly preferred are human non-dividing cells.

The transgene preferably encodes an immunogenic polypeptide. The method can further comprise harvesting or isolating the polypeptide.

The lentiviral vector or lentiviral particle vector preferably comprises an MHC class I, MHC Class II, or β2 microglobulin upstream promoter sequence. Preferably the vector further comprises an MHC class I or β2 microglobulin promoter.

In one embodiment, the invention encompasses a method for expressing a transgene comprising inserting an MHC class I, MHC Class II, or β2 microglobulin upstream promoter sequence into a lentiviral vector and transducing a cell with the vector containing the MHC class I, MHC Class II, or β2 microglobulin upstream promoter sequence.

Therapeutic Use of Lentiviral Vectors

The present invention further relates to the use of the lentiviral vectors according to the invention, especially in the form of lentiviral particle vectors, for the preparation of therapeutic compositions or vaccines which are capable of inducing or contributing to the occurrence or improvement of an immunogical reaction against epitopes, more particularly those encoded by the transgene present in the vectors containing an MHC class I, MHC Class II, or β2 microglobulin upstream promoter sequence.

The present invention thus provides vectors that are useful as a medicament or vaccine, particularly for gene therapy.

These vectors are preferentially used for the treatment or prophylaxis of infectious diseases, especially diseases associated with virus infection and more particularly, with retrovirus infection, such as AIDS and other immunodeficiencies.

The invention can also be used in treatment protocols against tumors and cancers and especially could be used in protocols for immunotherapy or vaccination therapy against tumors.

As the vectors of the invention more specifically target dendritic cells to obtain a cell-mediated immune response and especially the CTL response associated with the antigen expressed by the transgene in these cells, they are particularly useful as vaccines targeting slow or endogenous pathogenic microorganisms such as Mycobacteria or HIV virus.

Accordingly, the invention relates to an immunogenic composition comprising a lentiviral vector as previously defined.

The immunogenic compositions of the invention preferably contain cPPT and CTS sequences in the vector and vector particles to induce or to stimulate the nuclear import of the vector genome in the target cells.

During reverse transcription, cPPT and CTS sequences induce the formation of a three stranded DNA structure referred as DNA triplex, which stimulates the nuclear import of DNA vector sequence. Preferably, the vector comprises a transgene and regulatory signals of retrotranscription, expression and encapsidation of retroviral or retroviral-like origin, wherein the composition is capable of inducing or of stimulating a CTL (Cytotoxic T Lymphocytes) or a CD4 response against one or several epitopes encoded by the transgene sequence present in the vector.

The titer of the lentiviral vector is improved by inclusion of an MHC class I, MHC Class II, or β2 microglobulin upstream promoter sequence in the vector.

Thus, the lentiviral vectors according to the invention have the ability to induce, improve, or in general be associated with the occurrence of a memory CTL response. In other words, they can be used for the preparation of therapeutic composition for the treatment of tumor diseases or infectious diseases, by induction of, stimulation of, or participation in the occurrence of a cell-mediated immune response, especially a CTL response or a memory response.

The lentiviral vectors of the invention can be used in methods of treatment and methods of inducing an immune response comprising administering the lentiviral vector to a host and generating a specific immune response against the transgene in the host. The cells and antibodies generated in these hosts can be used as diagnostic reagents.

The lentiviral vectors according to the invention can be directly administered to a patient through known routes of administration, including systemic, local, or cutaneous, intramuscular, intradermal, for instance intratumoral, administration routes. Ex vivo administration, for instance ex vivo transduction of target cells followed by administration of the treated cells to the patient to be treated, is also encompassed by the invention.

In a particular embodiment, the immunogenic composition according to the invention can be directly administered to the patient, in such a way that it will induce, improve, or participate in vivo in the occurrence of a cell-mediated immune response, especially a CTL-mediated immune response.

In another embodiment, the immunogenic compositions are used once or upon repeated administrations so that they can enable the occurrence of a long-term memory cell mediated response.

The immunogenic compositions of the invention can be used to elicit or stimulate a cell-mediated immune response against multiple epitopes encoded by the nucleotides sequences of interest or transgene present in the vector or vector particles, and they can also be used to elicit or stimulate a cell-mediated immune response against the product of the entire sequence of a gene, for instance a gene of a pathogenic agent or fragments of said gene capable to encode at least 8 to 15 amino acids preferably 9 to 12 amino acids.

The invention also encompasses a lentiviral vector comprising a nucleotide sequence encoding a multiple repeat (at least 2 identical sequences) of said amino acid sequence inducing a cellular response and/or an amino acid sequence containing at least 2 different sequences corresponding to 2 epitopes of different pathogens or tumoral antigens.

As a result, the invention encompasses a composition that could be used in prophylactic and/or therapeutic vaccination protocols, for the treatment of tumors and especially as anti-cancer or anti-infectious diseases treatment.

In particular, it can be used in combination with adjuvants, other immunogenic compositions, chemotherapy, or any other therapeutic treatment.

Having thus described different embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein.

EXAMPLES

Example 1

Cell Lines

HEK 293T (human embryonic kidney cell line, ATCC CRL-11268, (Graham et al. 1977)) cells were maintained in Dubelcco's modified Eagle's medium (DMEM/High modified, Hyclone) supplemented with 10% fetal bovine serum (FBS, PAA), 1% L-Glutamine (Eurobio), 1% Penicillin-Streptomycin (Gibco by Life technologies) and 1% Sodium Pyruvate (Gibco by Life technologies).). The cell line was kept in an incubator with humidified atmosphere of 5% $CO_2$ at 37° C.

Example 2

Plasmids Construction

The promoters are cloned between the MluI and BamHI sites of the pFLAP-GFP proviral plasmid.

β2m_Upstream sequence (β2m_US) cloned upstream of the promoters:

HLA-B7 and HLA-E promoters were purchased from GeneArt (Lifetechnologies), and they were designed to encompass the β2m upstream promoter sequence (β2m_US) upstream the 5'end of the original promoter sequence. To generate the HLA-B7 and HLA-E provirus plasmids, PCR reactions were performed to only amplify the wild type promoter sequences, which were cloned between the MluI and BamHI sites of the pFlap-GFP plasmid.

To add the β2m-upstream sequence (β2m_US) in the 5' end of the HLA-A2, HLA-DRα, CMV and UBC promoters, we performed fusion PCR reactions. Briefly, three separate PCR reactions were performed: the first PCR amplify the β2m_US, the second PCR amplify the promoter, including a 25 bp overhang homologous to the end of the β2m_US. The PCR 1 and 2 products are then purified in an agarose gel (QIAquick gel extraction kit, QIAGEN) and used as matrices for the third PCR that will generate the final DNA product (β2m_US-Promoter). Primers used for the three PCR of each promoter are resumed in table 1. The PCR 3 product are gel purified and cloned in pCR®2.1-TOPO® (Life Technologies), sequenced, digested by MluI and BamHI restriction enzymes and cloned into the pFlap-GFP.

β2m_Upstream sequence cloned upstream the promoters, in reverse orientation:

The β2m upstream promoter sequence in reverse orientation (β2m_USR) was cloned upstream each promoter using fusion PCR as described above. All the USR_promoters were amplified between AscI and BamHI sites and then cloned into the pflap-GFP using MluI and BamHI sites. Primers used for the three PCR of each promoter are listed in table 2.

β2m_Upstream sequence cloning downstream the GFP in direct orientation:

β2m_US was cloned downstream the GFP reporting gene using XhoI and KpnI restriction sites. First, a PCR was performed to add the XhoI and KpnI sites in 5' and 3' of the β2m_US respectively. Primers used for the PCR are: forward: 5'-CTCGAGGAGAAACCCTGCAGGGAATTC-3' (SEQ ID NO:9), reverse: 5'-GGTACCGAGTCTCGTGATGTTTAAGAAGGCA-3' (SEQ ID NO:10). The PCR products were gel purified, cloned in pCR®2.1-TOPO® (LifeTechnologies), sequenced, digested by XhoI and KpnI restriction enzymes and cloned between the XhoI and KpnI sites of the pFlap-GFP.

β2m_Upstream sequence cloned downstream the GFP in reverse orientation:

The β2m upstream promoter sequence in reverse orientation (β2m_USR) was cloned downstream the GFP reporting gene using XhoI and KpnI restriction sites. First, a PCR was realized to add the XhoI and KpnI sites in 5' and 3' of the β2m_USR respectively. Primers used for the PCR are: forward: 5'-GGTACCGAGAAACCCTGCAGGGAATTCCCCAG-3' (SEQ ID NO:11) reverse: 5'-CTCGAGGAGTCTCGTGATGTTTAAGAAGGCA-3' (SEQ ID NO:12). The PCR product is then gel purified, cloned in pCR®2.1-TOPO® (LifeTechnologies), sequenced, digested by XhoI and KpnI restriction enzymes and cloned between the XhoI and KpnI of the pFlap.

β2m_Upstream sequence cloned between pUCori et KanR:

As the number of restrictions sites present between the pUCori and KanR sequences is restrained, we chose to clone the β2m_US into the PmlI sites. As a PmlI site is also present in the 5'LTR of the pFlap backbone, we first added the β2m_US upstream the pUCori using fusion PCR and then cloned the whole fragment between the two PmlI sites. Primers used for PCR1 (amplification of β2m_US) are: F1_5'-CACGTGGAGAAACCCTGCAGGGAATTCCCCAG-3' (SEQ ID NO:13) and R1_5'-GAGTCTCGTGATGTTTAAGAAGGCA-3' (SEQ ID NO:14). Primers used for PCR2 (amplification of pUCori and SV40) are: F2_5-TGCCTTCTTAAACATCACGAGACTCCTAAAACTTCATTTTTAATTT-3' (SEQ ID NO:15), containing an overhang homologous to the end of β2m_US (in bold) and R2_5'-CACGTGATGAAATGCTAGGCGGCTGTC-3' (SEQ ID NO:16). PCR 1 and 2 products were purified on an agarose gel and used as matrices for the third PCR, and the F1 and R2 primers were used for the amplification. The PCR 3 product are gel purified and cloned in pCR®2.1-TOPO® (Life Technologies), sequenced, digested by PmlI and cloned between the same sites in the pFlap-GFP. Cloning orientation was controlled by enzymatic digestion.

β2m_Upstream sequence cloning between pUCori et KanR, in reverse orientation:

β2m_USR was cloned between the PmlI sites as described above. Primers used for PCR1 (amplification of β2m_USR) are: F1_5'-CACGTGGAGTCTCGTGATGTTTAAGAAGGCATG-3' (SEQ ID NO:17) and R1_5'-GAGAAACCCTGCAGGGAATTCCCCAG-3'(SEQ ID NO:18). Primers used for PCR2 (amplification of pUCori and SV40) are: F2_5-TGGGGAATTCCCTGCAGGGTTTCTCCTAAAACTTCATTTTTAATTT-3' (SEQ ID NO:19) containing an overhang homologous to the end of β2m_USR (in bold) and R2_5'-CACGTGATGAAATGCTAGGCGGCTGTC-3' (SEQ ID NO:20). PCR 1 and 2 products were gel purified and used as matrice for the third PCR, and the F1 and R2 primers were used for the amplification. The PCR 3 product are gel purified and cloned in pCR®2.1-TOPO® (LifeTechnologies), sequenced, digested by PmlI and cloned between the same sites in the pFlap-GFP. Cloning orientation was controlled by enzymatic digestion.

The promoters were cloned into the pFlap-GFP plasmid using the MluI and BamHI sites. As β2m and HLA-B7 promoters contain a MluI site in their sequence, an AscI site (compatible with MluI site) is used as replacement, which makes the MluI site disappear.

Short Upstream Sequences Cloned Upstream of the Promoters

HLA-A2, HLA-E and HLA-DRα short upstream sequences were purchased from GeneArt and cloned upstream their respective promoters using MluI restriction site. Orientation of the inserted sequences was controlled by sequencing. The HLA-B7 short upstream sequence was added upstream of the HLA-B7 promoter using fusion PCR Primers used for PCR1 (amplification of HLA-B7_US) are: F1_5'-GGCGCGCCCAGGTTTAAAGAGAAAAC-CCCTG-3' (SEQ ID NO:17) and R1_5'-ATTGCA-GACGCGGCCCTCGGAGCCTGAGA-3' (SEQ ID NO:18). Primers used for PCR2 (amplification of HLA-B7 promoter) are: F2_5-AGGCTCCGAGGGCCGCGTCTG-CAATGGGGAGGCGCACGTTGGGGATTC-3' (SEQ ID NO:19) containing an overhang homologous to the end of HLA-B7_US (in bold) and R2_5'-CGGAAGGAAAGT-GACGGGCGAA-3' (SEQ ID NO:20). PCR 1 and 2 products were gel purified and used as matrice for the third PCR, and the F1 and R2 primers were used for the amplification. The PCR 3 product are gel purified and cloned in pCR®2.1-TOPO® (Life Technologies), sequenced, digested by MluI and BamHI restriction enzymes and cloned into the pFlap-GFP.

Long Upstream Sequences Cloned Upstream of the Promoters

HLA-A2, HLA-E and HLA-DRα long upstream sequences were purchased from GeneArt and cloned upstream their respective promoters using MluI restriction site. Orientation of the inserted sequences was controlled by sequencing. B2m_Up and HLA-B7_Up blocks (promoters+ long upstream sequences) were purchased from GeneArt and cloned in the pFlap-GFP using the MluI/BamHI restrictions sites.

Double Upstream Sequences

HLA-E_US was cloned in the pFlap-ΔU3-β2m_E_US-GFP upstream of the GFP gene using XhoI and KpnI restriction sites. First, a PCR was realized to add the XhoI and KpnI sites in 5' and 3' of the HLA-E_US respectively. Primers used for the PCR are: forward: 5'-CTCGA-GACTAATTTCTTTTTCTTGTTGCC-3' and reverse: 5'-GGTACCAACTTTTAGGTTTCGGTATCTCTGCACA-3. The PCR product is then gel purified, cloned in pCR®2.1-TOPO® (Life Technologies), sequenced, digested by XhoI and KpnI restriction enzymes and cloned between the same sites in the pFlap-ΔU3-β2m_E_US-GFP, allowing the obtaining of the pFlap-ΔU3-β2m_E_US-GFP_E_US.

Example 3

Lentiviral Production

The lentiviral vectors were produced by transient transfection of HEK 293T cells using a standard calcium phosphate precipitation protocol. HEK 293T cells were seeded at $7 \times 10^6$ cells in 10 cm$^2$ Tissue Culture Dish (BD Falcon) in 10 mL of complete culture medium and maintained 24 h in an incubator with humidified atmosphere of 5% $CO_2$ at 37° C. to adhere. For each vector produced, one tissue culture dish is transfected as following: the lentiviral backbone plasmid pFlap (10 µg), the pThV-Env1 encoding envelope plasmid (2 µg), and the pThV-GP packaging plasmid (10 µg) were mixed with 353 µL of sterile distilled water (Gibco by Life Technologies) and 125 µL of $CaCl_2$ (Fluka). The DNA mix is then added drop to drop to 500 µL of 37° C. prewarmed HBS 2× pH=7.3 and the 1 mL of precipitate obtained was added to the culture medium of the cells. The transfected cells were then incubated at 37° C., 5% $CO_2$. The medium was replaced 24 h after transfection by 7 mL of harvest medium without serum and the viral supernatant was harvested after an additional 24 h, clarified by centrifugation 5 min. at 2500 rpm and stored à −20° C.

Example 4

Quantification of Lentiviral Vectors by Flow Cytometry

For the quantification of infective particles, HEK 293T cells were seeded in 24-well plates (BD Falcon) at a density of $1\times10^5$ cells per well in complete medium containing 10% FBS and incubated for 4 h to adhere. The cells were transduced by replacing the medium with 300 µl of dilutions 1/100, 1/300 and 1/900 of viral samples in complete medium, followed by incubation at 37° C., 5% $CO_2$ for 2 h. After adsorption, 1 mL of complete medium was added to each well. At 72 h posttransduction, the cells were trypsinized and resuspended in 300 µL of complete medium, and the percentage of cells expressing GFP was determined with a FACScalibur flow cytometer (BD Biosciences), using the FL1 channel. Two sets of three dilutions were performed for each sample tested. The values corresponding to a percentage of transduced cells less than 30% were used to calculate the approximate number of transducing units (TU) present in the viral suspension.

$$\text{Titer}(TU/mL) = \frac{(\% \text{ transduced cells} \times 1.10^5)}{100} \times \frac{1000 \times \text{dilution factor}}{300}$$

Example 5

Quantification of Total Produced Particles by ELISA p24

The quantification of total particles was performed on dilutions $10^{-5}$, $10^{-6}$ and $10^{-7}$ of each production supernatant, using a commercial kit (Perkin Elmer), following the manufacturer's recommendations.

Example 6

Quantification of Efficient Produced Particles by qPCR

HEK 293T cells were seeded in 6-well plates (BD Falcon) in culture medium and incubated for 4 h at 37° C., 5% CO2 in moist atmosphere. Cells were transduced with 3 successive dilutions of lentiviral vector (1/5, 1/10 and 1/20). 72 h post-incubation, cells were harvested and transduced HEK 293T cell pellets were realized. After intermediate storage at −20° C., total genomic DNA from transduced cell-pellets was extracted using a method based on QIAGEN QIAamp DNA mini kit handbook using single columns and a microcentrifuge. Extracted DNA was stored at −20° C. till used in qPCR. Quantification of the proviral DNA integrated in the host genome was performed on extracted DNA using an optimized Taqman qPCR, based on the exonuclease activity of the 5'-3' Taq polymerase.

The probe is an oligonucleotide specific to the backbone of our lentiviral vector' sequence. The amplification is performed with a polymerase Master Mix (Fermentas Thermo Scientific) and using Flap A primer (CCCAAGAACCCAAGGAACA) (SEQ ID NO:21), Flap S primer (AGACAA GATAGAGGAAGAGCAAAAC) (SEQ ID NO:22), and Lenti TM probe (6FAM-AACCATTAG-GAGTAGCACCCACCAAGG-BBQ) (SEQ ID NO:23). In order to normalize the number of integrations to the number of cells harvested a specific amplification of cellular ACTIN gene is applied in parallel using the same Master Mix and Actine A primer (CGGTGAGGATCTTCATGAGGTAGT) (SEQ ID NO:24), Actine S primer (AACACCCCAGCCAT-GTACGT) (SEQ ID NO:25) and Humura ACT TM probe (6FAM-CCAGCCAGGTCCAGACGCAGGA-BBQ) (SEQ ID NO:26). Both reactions are achieved on MasterCycler Ep Realplex S (Eppendorf) following the thermal program (2 min at 50° C., 10 min at 95° C. and 40 cycles of 15 seconds at 95° C. and 1 min at 63° C.). The analysis is performed on MasterCycler Ep Realplex Software.

SEQUENCE LISTING

```
<160> NUMBER OF SEQ ID NOS: 46

<210> SEQ ID NO 1
<211> LENGTH: 300
<212> TYPE: DNA
<213> ORGANISM: Homo sapiens

<400> SEQUENCE: 1
agaagttctc cttctgctag gtagcattca aagatcttaa tcttctgggt ttccgttttc    60
tcgaatgaaa aatgcaggtc cgagcagtta actggcgggg gcaccattag caagtcactt   120
agcatctctg gggccagtct gcaaagcgag ggggcagcct taatgtgcct ccagcctgaa   180
gtcctagaat gagcgcccgg tgtcccaagc tgggcgcgc accccagatc ggagggcgcc    240
gatgtacaga cagcaaaactc acccagtcta gtgcatgcct tcttaaacat cacgagactc   300
```

<210> SEQ ID NO 2
<211> LENGTH: 300
<212> TYPE: DNA
<213> ORGANISM: Homo sapiens

<400> SEQUENCE: 2

```
ctggagggca atggcacgat cttggctcac cgcaacctcc tcctcctggg ttcaagtgat      60
tctcctgcct cagcctccca agtagccagg attacagcca tgcgccacca cgccggctaa     120
ttttttggac ttttagtaga cagggtttt ctccatattg gtcgggctgg tctcgaactc      180
ccaacctcag gtgatcagcc cgccttggcc tcccaaagtg ctgagattac aggcgtgagc     240
caccgcgccc agccaggact aatttctaag agtgtgcaga gataccgaaa cctaaaagtt    300
```

<210> SEQ ID NO 3
<211> LENGTH: 300
<212> TYPE: DNA
<213> ORGANISM: Homo sapiens

<400> SEQUENCE: 3

```
actctctggc atcaagttcc ccgtgctcag tttccctaca caagagtcca agaggagagg      60
taaggagtgg gaggcaggga gtccagttca gggacaggga ttccaggacg agaagtgaag     120
gggaaggggc tgggcgcagc ctggggggtct ctccctggtt tccacagaca gatccttgtc     180
caggactcag gcagacagtg tgacaaagag gcttggtgta ggagaagagg gatcaggacg     240
aagtcccagg tcccggacgg ggctctcagg gtctcaggct ccgagggccg cgtctgcaat     300
```

<210> SEQ ID NO 4
<211> LENGTH: 300
<212> TYPE: DNA
<213> ORGANISM: Homo sapiens

<400> SEQUENCE: 4

```
caaggggaga ggtaagtgtc ctttattttg ctggatgtag tttaatatta cctgaggtaa      60
ggtaaggcaa agagtgggag gcagggagtc cagttcaggg acggggattc caggagaagt     120 gaagggggaag gggctgggcg cagcctgggg gtctctccct ggtttccaca gacagatcct    180
tggccaggac tcaggcacac agtgtgacaa agatgcttgg tgtaggagaa gagggatcag     240
gacgaagtcc caggtcccgg gcggggttct cagggtctca ggctccaagg gccgtgtctg     300
```

<210> SEQ ID NO 5
<211> LENGTH: 300
<212> TYPE: DNA
<213> ORGANISM: Homo sapiens

<400> SEQUENCE: 5

```
ttcattgtct ggcaccaagc tccttggggt gaattttctt ccaaaagagt ccggggagtc      60
caggtatgga atgggaggca gaaagttcaa tcaaggggact gggatttcgg aatgaataat    120
gaagggagat ggactgggtc catgccgaag gtttctccct ggtttctcag cccccgggcg     180
aagactcagg gagacattga gacacaccct gcacaggagg gggagggggga ggggagggc     240 aaagtcccag ggccccagga gtggctctca agggctcagg ccccgaggcg gtgtctgggg    300
```

<210> SEQ ID NO 6
<211> LENGTH: 300
<212> TYPE: DNA
<213> ORGANISM: Homo sapiens

<400> SEQUENCE: 6

```
gctcactctc tggcaacaag ctccctgggg tgattttcct tctagaagag tacaggagga    60
caggcaagga gtgggaggca gggagtccag ttcagggaca gggattccgg gatgaaaagt   120
gaagggagag ggccagggac cttgccgagg gtttctccct ggtttctcag acagctcctg   180
ggccaagact cagggagaca ctgagacaga acgcttggca caagagtagc ggggtcaggg   240
cgaagtccca gggcctcaag cgtggctctc agggtctcag ccccacagg cggtgtatgg    300
```

```
<210> SEQ ID NO 7
<211> LENGTH: 300
<212> TYPE: DNA
<213> ORGANISM: Homo sapiens

<400> SEQUENCE: 7
```

```
gcttactctc tggcaccaaa ctccatggga tgattttcct tctagaagag tccaggtgga    60
caggtaagga gtgggagtca gggagtccag ttccagggac agagattacg ggataaaaag   120
tgaaaggaga gggacggggc ccatgccgag ggtttctccc ttgtttctca gacagctctt   180
gggccaagac tcagggagac attgagacag agcgcttggc acagaagcag aggggtcagg   240
gcgaagtcca gggccccagg cgttggctct cagggtctca ggccccgaag gcggtgtatg   300
```

```
<210> SEQ ID NO 8
<211> LENGTH: 316
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(57)
```

-continued

```
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t
<220> FEATURE:
<221> NAME/KEY: misc_feature
<222> LOCATION: (102)..(103)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (222)..(224)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
```

```
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (293)..(295)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t

<400> SEQUENCE: 8
gntnantntc tggcancaan ctccntgggn tgagtttnct tctacaagag tccangnagg      60
acaggtaagg agtgggangg cagggagtcc agttncnagg gnnacaggga ttccgggann     120
agaagtgaag ggnnagggnc tgggnccatn cngagggttt ctccctggtt tctncagaca    180
gnnctcctng gccaagactc aggnagacan tgngacanag cnnngcttgg ngcaggnagn    240 agagggtca ggncgaagtc ccaggnccnc aggcgtnggc tctcagggtc tcnnaggcn     300 ccgaaggcng tgtntg                                                   316

<210> SEQ ID NO 9
<211> LENGTH: 27
<212> TYPE: DNA
<213> ORGANISM: Artificial Sequence
<220> FEATURE:
<223> OTHER INFORMATION: PCR Primer

<400> SEQUENCE: 9
ctcgaggaga aaccctgcag ggaattc                                        27

<210> SEQ ID NO 10
<211> LENGTH: 31
<212> TYPE: DNA
<213> ORGANISM: Artificial Sequence
<220> FEATURE:
<223> OTHER INFORMATION: PCR Primer

<400> SEQUENCE: 10
ggtaccgagt ctcgtgatgt ttaagaaggc a                                   31

<210> SEQ ID NO 11
```

<211> LENGTH: 32
<212> TYPE: DNA
<213> ORGANISM: Artificial Sequence
<220> FEATURE:
<223> OTHER INFORMATION: PCR Primer

<400> SEQUENCE: 11
ggtaccgaga aaccctgcag ggaattcccc ag                                  32

<210> SEQ ID NO 12
<211> LENGTH: 31
<212> TYPE: DNA
<213> ORGANISM: Artificial Sequence
<220> FEATURE:
<223> OTHER INFORMATION: PCR Primer

<400> SEQUENCE: 12
ctcgaggagt ctcgtgatgt ttaagaaggc a                                   31

<210> SEQ ID NO 13
<211> LENGTH: 32
<212> TYPE: DNA
<213> ORGANISM: Artificial Sequence
<220> FEATURE:
<223> OTHER INFORMATION: PCR Primer

<400> SEQUENCE: 13
cacgtggaga aaccctgcag ggaattcccc ag                                  32

<210> SEQ ID NO 14
<211> LENGTH: 25
<212> TYPE: DNA
<213> ORGANISM: Artificial Sequence
<220> FEATURE:
<223> OTHER INFORMATION: PCR Primer

<400> SEQUENCE: 14
gagtctcgtg atgtttaaga aggca                                          25

<210> SEQ ID NO 15
<211> LENGTH: 46
<212> TYPE: DNA
<213> ORGANISM: Artificial Sequence
<220> FEATURE:
<223> OTHER INFORMATION: PCR Primer

<400> SEQUENCE: 15
tgccttctta aacatcacga gactcctaaa acttcatttt taattt                   46

<210> SEQ ID NO 16
<211> LENGTH: 27
<212> TYPE: DNA
<213> ORGANISM: Artificial Sequence
<220> FEATURE:
<223> OTHER INFORMATION: PCR Primer

<400> SEQUENCE: 16
cacgtgatga aatgctaggc ggctgtc                                        27

<210> SEQ ID NO 17
<211> LENGTH: 33
<212> TYPE: DNA
<213> ORGANISM: Artificial Sequence
<220> FEATURE:
<223> OTHER INFORMATION: PCR Primer

<400> SEQUENCE: 17

```
cacgtggagt ctcgtgatgt ttaagaaggc atg                              33
```

<210> SEQ ID NO 18
<211> LENGTH: 26
<212> TYPE: DNA
<213> ORGANISM: Artificial Sequence
<220> FEATURE:
<223> OTHER INFORMATION: PCR Primer

<400> SEQUENCE: 18

```
gagaaaccct gcagggaatt ccccag                                      26
```

<210> SEQ ID NO 19
<211> LENGTH: 46
<212> TYPE: DNA
<213> ORGANISM: Artificial Sequence
<220> FEATURE:
<223> OTHER INFORMATION: PCR Primer

<400> SEQUENCE: 19

```
tggggaattc cctgcagggt ttctcctaaa acttcatttt taattt                46
```

<210> SEQ ID NO 20
<211> LENGTH: 27
<212> TYPE: DNA
<213> ORGANISM: Artificial Sequence
<220> FEATURE:
<223> OTHER INFORMATION: PCR Primer

<400> SEQUENCE: 20

```
cacgtgatga aatgctaggc ggctgtc                                     27
```

<210> SEQ ID NO 21
<211> LENGTH: 19
<212> TYPE: DNA
<213> ORGANISM: Artificial Sequence
<220> FEATURE:
<223> OTHER INFORMATION: PCR Primer

<400> SEQUENCE: 21

```
cccaagaacc caaggaaca                                              19
```

<210> SEQ ID NO 22
<211> LENGTH: 19
<212> TYPE: DNA
<213> ORGANISM: Artificial Sequence
<220> FEATURE:
<223> OTHER INFORMATION: PCR Primer

<400> SEQUENCE: 22

```
gatagaggaa gagcaaaac                                              19
```

<210> SEQ ID NO 23
<211> LENGTH: 27
<212> TYPE: DNA
<213> ORGANISM: Artificial Sequence
<220> FEATURE:
<223> OTHER INFORMATION: Lenti TM probe

<400> SEQUENCE: 23

```
aaccattagg agtagcaccc accaagg                                     27
```

<210> SEQ ID NO 24
<211> LENGTH: 24
<212> TYPE: DNA

```
<213> ORGANISM: Artificial Sequence
<220> FEATURE:
<223> OTHER INFORMATION: Actine A primer

<400> SEQUENCE: 24
cggtgaggat cttcatgagg tagt                                              24

<210> SEQ ID NO 25
<211> LENGTH: 20
<212> TYPE: DNA
<213> ORGANISM: Artificial Sequence
<220> FEATURE:
<223> OTHER INFORMATION: Actine S primer

<400> SEQUENCE: 25
aacaccccag ccatgtacgt                                                   20

<210> SEQ ID NO 26
<211> LENGTH: 22
<212> TYPE: DNA
<213> ORGANISM: Artificial Sequence
<220> FEATURE:
<223> OTHER INFORMATION: Humura ACT TM probe

<400> SEQUENCE: 26
ccagccaggt ccagacgcag ga                                                22

<210> SEQ ID NO 27
<211> LENGTH: 330
<212> TYPE: DNA
<213> ORGANISM: Homo sapiens

<400> SEQUENCE: 27
gagaaaccct gcagggaatt ccccagctgt agttataaac agaagttctc cttctgctag       60
gtagcattca aagatcttaa tcttctgggt ttccgttttc tcgaatgaaa aatgcaggtc      120
cgagcagtta actggcgggg gcaccattag caagtcactt agcatctctg ggccagtct       180 gcaaagcgag ggggcagcct taatgtgcct ccagcctgaa gtcctagaat gagcgcccgg      240
tgtcccaagc tggggcgcgc accccagatc ggagggcgcc gatgtacaga cagcaaactc      300
acccagtcta gtgcatgcct tcttaaacat                                       330

<210> SEQ ID NO 28
<211> LENGTH: 1058
<212> TYPE: DNA
<213> ORGANISM: Homo sapiens

<400> SEQUENCE: 28
cttccaagat ctctgcccct ccccatcgcc atggtccact tcctcttctc actgttcctc       60
ttagaaaaga tctgtggact ccaccaccac gaaatggcgg caccttattt atggtcactt      120
tagagggtag gttttcttaa tgggtctgcc tgtcatgttt aacgtccttg gctgggtcca      180
aggcagatgc agtccaaact ctcactaaaa ttgccgagcc ctttgtcttc cagtgtctaa      240
aatattaatg tcaatggaat caggccagag tttgaattct agtctcttag cctttgtttc      300
ccctgtccat aaaatgaatg ggggtaattc tttcctccta cagtttattt atatattcac      360
taattcattc attcatccat ccattcgttc attcggttta ctgagtacct actatgtgcc      420
agcccctgtt ctagggtgga aactaagaga atgatgtacc tagagggcgc tggaagctct      480
aaagccctag cagttactgc ttttactatt agtggtcgtt ttttctccc cccgccccc       540 cgacaaatca acagaacaaa gaaaattacc taaacagcaa ggacataggg aggaacttct      600
```

```
tggcacagaa ctttccaaac acttttttcct gaagggatac aagaagcaag aaaggtactc    660
tttcactagg accttctctg agctgtcctc aggatgcttt tgggactatt tttcttaccc    720
agagaatgga gaaaccctgc agggaattcc caagctgtag ttataaacag aagttctcct    780
tctgctaggt agcattcaaa gatcttaatc ttctgggttt ccgttttctc gaatgaaaaa    840
tgcaggtccg agcagttaac tggctggggc accattagca agtcacttag catctctggg    900
gccagtctgc aaagcgaggg ggcagcctta atgtgcctcc agcctgaagt cctagaatga    960
gcgcccggtg tcccaagctg gggcgcgcac cccagatcgg agggcgccga tgtacagaca   1020
gcaaactcac ccagtctagt gcatgccttc ttaaacat                           1058

<210> SEQ ID NO 29
<211> LENGTH: 322
<212> TYPE: DNA
<213> ORGANISM: Homo sapiens

<400> SEQUENCE: 29
tacacctcca ttcccagagc aagcttactc tctggcacca aactccatgg gatgattttt     60
cttctagaag agtccaggtg gacaggtaag gagtgggagt cagggagtcc agttccaggg    120
acagagatta cgggataaaa agtgaaagga gagggacggg gcccatgccg agggtttctc    180
ccttgtttct cagacagctc ttgggccaag actcagggag acattgagac agagcgcttg    240
gcacagaagc agaggggtca gggcgaagtc cagggcccca ggcgttggct ctcagggtct    300
caggccccga aggcggtgta tg                                             322

<210> SEQ ID NO 30
<211> LENGTH: 531
<212> TYPE: DNA
<213> ORGANISM: Homo sapiens

<400> SEQUENCE: 30
gagtcctgtt gtaatgcttt tggacacatt tatacattaa ggggccaaag tcacattttt     60
tacctattag attcctgatc attcaggggt taccaagatt ctgctaccca ctgtagttaa    120
taaacaaaga gcaaattggt tctctattctg tctcatgcac tcaggcacaa cttttccgga    180
ttaaaaacaa aaacaacaac aacaaaaatc tacacctcca ttcccagatc aagcttactc    240
tctggcacca aactccatgg ggtgattttt cttctagaag agtccaggtg gacaggtaag    300
gagtgggagt cagggagtcc agttcaggga cagagataat gggatgaaaa gtgaaaggag    360
agggacgggg cccatgccga gggtttctcc cttgtttctc agacagctcc tgggccaaga    420
ctcagggaga cattgagaca gagcgcttcg cacaggagca gaggggtcag ggcgaagtcc    480
cagggcccca ggcgtggctc tcagagtctc aggccccgaa ggcggtgtat g             531

<210> SEQ ID NO 31
<211> LENGTH: 352
<212> TYPE: DNA
<213> ORGANISM: Homo sapiens

<400> SEQUENCE: 31
aggtttaaag agaaaacccc tgtctctaca cctccattcc cagggcgagc tcactctctg     60
gcatcaagtt ccccgtgctc agtttcccta cacaagagtc caagaggaga ggtaaggagt    120
gggaggcagg gagtccagtt cagggacagg gattccagga cgagaagtga aggggaaggg    180
gctgggcgca gcctgggggt ctctccctgg tttccacaga cagatccttg tccaggactc    240
```

```
aggcagacag tgtgacaaag aggcttggtg taggagaaga gggatcagga cgaagtccca    300
ggtcccggac ggggctctca gggtctcagg ctccgagggc cgcgtctgca at            352
```

<210> SEQ ID NO 32
<211> LENGTH: 511
<212> TYPE: DNA
<213> ORGANISM: Homo sapiens

<400> SEQUENCE: 32

```
gagtttaatt gtaatgctgt tttgacacag gtcttttaca aattggaatt ctaatcattc     60
agggattacc aatattgtgc tacctactgt attaacaaac aaaaaggaaa ctggtctcta    120
tgagaatccc tatgcggtgc cttcagagaa aacttcacca ggtttaaaga gaaaacccct    180
gtctctacac ctccattccc agggcgagct cactctctgg catcaagttc cccgtgctca    240
gtttccctac acaagagtcc aagaggagag gtaaggagtg ggaggcaggg agtccagttc    300
agggacaggg attccaggac gagaagtgaa ggggaagggg ctgggcgcag cctggggggtc   360 tctccctggt ttccacagac agatccttgt ccaggactca ggcagacagt gtgacaaaga    420
ggcttggtgt aggagaagag ggatcaggac gaagtcccag gtcccggacg ggctctcag     480 ggtctcaggc tccgagggcc gcgtctgcaa t                                   511
```

<210> SEQ ID NO 33
<211> LENGTH: 328
<212> TYPE: DNA
<213> ORGANISM: Homo sapiens

<400> SEQUENCE: 33

```
actaatttct tttttcttgt tgcccaggct ggagggcaat ggcacgatct ggctcaccg      60 caacctcctc ctcctgggtt caagtgattc tcctgcctca gcctcccaag tagccaggat    120
tacagccatg cgccaccacg ccggctaatt ttttggactt ttagtagaga cagggtttct    180
ccatattggt cgggctggtc tcgaactccc aacctcaggt gatcagcccg ccttggcctc    240
ccaaagtgct gagattacag gcgtgagcca ccgcgcccag ccaggactaa tttctaagag    300
tgtgcagaga taccgaaacc taaaagtt                                        328
```

<210> SEQ ID NO 34
<211> LENGTH: 1047
<212> TYPE: DNA
<213> ORGANISM: Homo sapiens

<400> SEQUENCE: 34

```
tttttttcccc ctagacatct cactctgtcg cccaggctgg agtgcagtgg tgtgatctcg    60
gctcactgca accaccacct tcgggttca agcaattctc ctatctcagc ctccagagtt     120
gctggaatta caggcgcgca ccaccacacc cggctaattt ttgtattgtt agtagagaca    180
gggtttcatc atgttggcca ggttagtctt gaactcctga cctcgtgatc tgcctgcctc    240
ggcctaccaa aatgctgcga ttacaggcgt gagccaccgt tcccggccta tacgttgttt    300
attttggaaa aattaaaaat taagtttttt ttcattaaag atatgttatt tccgatcaag    360
agatcaagac catcctggcc aacatggtga accccgtctc tactaaaaaa cacaaaaatt    420
agctgggtgt ggtggcacac gcctgtagtt ccagttactg gggaggctga ggcaggagaa    480
tcgcttgaac ccgggagaag gaggttgcag tgagccgaga tcatgccact gcactccagc    540
ctggggacag agcaagactc tgactcaaaa aaaaaaaaag ttgtttctat taacatgtaa    600
tgggttatta atattctctt aaatgaatta atattttaa tattttgttt taatatcttt     660
```

```
taatttatat atgataaaaa ttgatacaat ccacagaaac aaaatttatt tgggtcctca    720
ctaatttctt ttttcttgtt gcccaggctg gagggcaatg gcacgatctt ggctcaccgc    780
aacctcctcc tcctgggttc aagtgattct cctgcctcag cctcccaagt agccaggatt    840
acagccatgc gccaccacgc cggctaattt ttttggacttt tagtagagac agggtttctc    900
catattggtc gggctggtct cgaactccca acctcaggtg atcagcccgc cttggcctcc    960
caaagtgctg agattacagg cgtgagccac cgcgcccagc caggactaat ttctaagagt   1020
gtgcagagat accgaaacct aaaagtt                                       1047
```

<210> SEQ ID NO 35
<211> LENGTH: 356
<212> TYPE: DNA
<213> ORGANISM: Homo sapiens

<400> SEQUENCE: 35

```
atacagcctt tcatccttct ccagtgttga gagtgttgaa cctcagagtt tctcctctca     60
ttttctctaa atgagataca atgccagcca tcccaagctc ttggcctgag ttgatcatct    120
tgaagtctag gactccaaga agcatgaaag agcttcttta gtgaagctat gtcctcagta    180
ctgccaaaat tcagacaatc tccatggcct gacaatttac cttctatttg ggtaatttat    240
tgtcccttac gcaaactctc caactgtcat tgcacagaca tatgatctgt atttagctct    300
cactttaggt gtttccattg attctattct cactaatgtg cttcaggtat atccct        356
```

<210> SEQ ID NO 36
<211> LENGTH: 522
<212> TYPE: DNA
<213> ORGANISM: Homo sapiens

<400> SEQUENCE: 36

```
taggctttgc ccattatact ctctcatatt cattgacctg aatcctcaaa tgaggtgtgt     60
ccattagtca actccaatct cttgtcatat ataagatggt agagatgaga agaaggtagc    120
tcctttacag cccactattt ccactaacta ctacctgtgt ttcaagatac agcctttcat    180
ccttctccag tgttgagagt gttgaacctc agagtttctc ctctcatttt ctctaaatga    240
gatacaatgc cagccatccc aagctcttgg cctgagttgt tcatcttgaa gtctaggact    300
ccaagaagca tgaaagagct tctttagtga agctatgtcc tcagtactgc caaaattcag    360
acaatctcca tggcctgaca atttaccttc tatttgggta atttattgtc ccttacgcaa    420
actctccagc tgtcatggca cagacatatg atctgtattt agctctcact ttaggtgttt    480
ccattgattc tattctcact aatgtgcttc aggtatatcc ct                       522
```

<210> SEQ ID NO 37
<211> LENGTH: 543
<212> TYPE: DNA
<213> ORGANISM: Homo sapiens

<400> SEQUENCE: 37

```
tacacctcca ttcccagagc aagcttactc tctggcacca aactccatgg gatgattttt     60
cttctagaag agtccaggtg gacaggtaag gagtgggagt cagggagtcc agttccaggg    120
acagagatta cgggataaaa agtgaaagga gagggacggg gcccatgccg agggtttctc    180
ccttgtttct cagacagctc ttgggccaag actcagggag acattgagac agagcgcttg    240
gcacagaagc agaggggtca gggcgaagtc cagggcccca ggcgttggct ctcagggtct    300
```

```
caggccccga aggcggtgta tggattgggg agtcccagcc ttggggattc cccaactccg    360
cagtttcttt tctccctctc ccaacctatg tagggtcctt cttcctggat actcacgacg    420
cggacccagt tctcactccc attgggtgtc gggtttccag agaagccaat cagtgtcgtc    480
gcggtcgcgg ttctaaagtc cgcacgcacc caccgggact cagattctcc ccagacgccg    540
agg                                                                 543
```

<210> SEQ ID NO 38
<211> LENGTH: 550
<212> TYPE: DNA
<213> ORGANISM: Homo sapiens

<400> SEQUENCE: 38

```
caggtttaaa gagaaaaccc ctgtctctac acctccattc ccagggcgag ctcactctct     60
ggcatcaagt tccccgtgct cagtttccct acacaagagt ccaagaggag aggtaaggag    120
tgggaggcag ggagtccagt tcagggacag ggattccagg acgagaagtg aaggggaagg    180
ggctgggcgc agcctggggg tctctccctg gtttccacag acagatcctt gtccaggact    240
caggcagaca gtgtgacaaa gaggcttggt gtaggagaag agggatcagg acgaagtccc    300
aggtcccgga cggggctctc agggtctcag gctccgaggg ccgcgtctgc aatggggagg    360
cgcagcgttg ggattcccc actcccctga gtttcacttc ttctcccaac ttgtgtcggg     420
tccttcttcc aggatactcg tgacgcgtcc ccacttccca ctcccattgg gtattggata    480
tctagagaag ccaatcagcg tcgccgcggt cccagttcta aagtccccac gcacccaccc    540
ggactcagag                                                          550
```

<210> SEQ ID NO 39
<211> LENGTH: 533
<212> TYPE: DNA
<213> ORGANISM: Homo sapiens

<400> SEQUENCE: 39

```
actaatttct tttttcttgt tgcccaggct ggagggcaat ggcacgatct tggctcaccg     60
caacctcctc ctcctgggtt caagtgattc tcctgcctca gcctcccaag tagccaggat    120
tacagccatg cgccaccacg ccggctaatt ttttggactt ttagtagaga cagggtttct    180
ccatattggt cgggctggtc tcgaactccc aacctcaggt gatcagcccg ccttggcctc    240
ccaaagtgct gagattacag gcgtgagcca ccgcgcccag ccaggactaa tttctaagag    300
tgtgcagaga taccgaaacc taaaagttta agaactgctg attgctggga aactctgcag    360
tttcccgttc ctctcgtaac ctggtcatgt gtccttcttc ctggatactc atgacgcaga    420
ctcagttctc attcccaatg ggtgtcgggt ttctagagaa gccaatcagc gtcgccacga    480
ctcccgacta taaagtcccc atccggactc aagaagttct caggactcag agg          533
```

<210> SEQ ID NO 40
<211> LENGTH: 517
<212> TYPE: DNA
<213> ORGANISM: Homo sapiens

<400> SEQUENCE: 40

```
gagaaaccct gcagggaatt ccccagctgt agttataaac agaagttctc cttctgctag     60
gtagcattca aagatcttaa tcttctgggt ttccgttttc tcgaatgaaa aatgcaggtc    120
cgagcagtta actggcgggg gcaccattag caagtcactt agcatctctg gggccagtct    180
gcaaagcgag ggggcagcct taatgtgcct ccagcctgaa gtcctagaat gagcgcccgg    240
```

```
tgtcccaagc tggggcgcgc accccagatc ggagggcgcc gatgtacaga cagcaaactc      300
acccagtcta gtgcatgcct tcttaaacat cacgagactc taagaaaagg aaactgaaaa      360
cgggaaagtc cctctctcta acctggcact gcgtcgctgg cttggagaca ggtgacggtc      420
cctgcgggcc ttgtcctgat ggctgggca cgcgtttaat ataagtggag gcgtcgcgct       480
ggcgggcatt cctgaagctg acagcattcg ggccgag                               517
```

<210> SEQ ID NO 41
<211> LENGTH: 655
<212> TYPE: DNA
<213> ORGANISM: Homo sapiens

<400> SEQUENCE: 41

```
atacagcctt tcatccttct ccagtgttga gagtgttgaa cctcagagtt tctcctctca       60
ttttctctaa atgagataca atgccagcca tcccaagctc ttggcctgag ttgatcatct      120
tgaagtctag gactccaaga agcatgaaag agcttcttta gtgaagctat gtcctcagta      180
ctgccaaaat tcagacaatc tccatggcct acaatttac cttctatttg ggtaatttat       240
tgtcccttac gcaaactctc caactgtcat tgcacagaca tatgatctgt atttagctct      300
cactttaggt gtttccattg attctattct cactaatgtg cttcaggtat atccctgtct      360
agaagtcaga ttggggttaa agagtctgtc cgtgattgac taacagtctt aaatacttga      420
tttgttgttg ttgttgtcct gtttgtttaa gaactttact tctttatcca atgaacggag      480
tatcttgtgt cctggaccct ttgcaagaac ccttccccta gcaacagatg cgtcatctca      540
aaatattttt ctgattggcc aaagagtaat tgatttgcat tttaatggtc agactctatt      600
acaccccaca ttctcttttc ttttattctt gtctgttctg cctcactccc gagct           655
```

<210> SEQ ID NO 42
<211> LENGTH: 752
<212> TYPE: DNA
<213> ORGANISM: Homo sapiens

<400> SEQUENCE: 42

```
gagtcctgtt gtaatgcttt tggacacatt tatacattaa ggggccaaag tcacattttt       60
tacctattag attcctgatc attcaggggt taccaagatt ctgctaccca ctgtagttaa      120
taaacaaaga gcaaattggt ctctattctg tctcatgcac tcaggcacaa cttttccgga      180
ttaaaaacaa aaacaacaac aacaaaaatc tacacctcca ttcccagatc aagcttactc      240
tctggcacca aactccatgg ggtgattttt cttctagaag agtccaggtg acaggtaag       300 gagtgggagt cagggagtcc agttcaggga cagagataat gggatgaaaa gtgaaggag       360 agggacgggg cccatgccga gggtttctcc cttgtttctc agacagctcc tgggccaaga      420
ctcaggagga cattgagaca gagcgcttcg cacaggagca gaggggtcag ggcgaagtcc      480
cagggcccca ggcgtggctc tcagagtctc aggccccgaa ggcggtgtat ggattgggga      540
gtcccagcct tggggattcc ccaactccgc agtttctttt ctccctctcc caacctatgt      600
agggtccttc ttcctggata ctcacgacgc ggacccagtt ctcactccca ttgggtgtcg      660
ggtttccaga gaagccaatc agtgtcgtcg cggtcgcggt tctaaagtcc gcacgcaccc      720
accgggactc agattctccc cagacgccga gg                                    752
```

<210> SEQ ID NO 43
<211> LENGTH: 707
<212> TYPE: DNA

<213> ORGANISM: Homo sapiens

<400> SEQUENCE: 43

```
gagtttaatt gtaatgctgt tttgacacag gtcttttaca aattggaatt ctaatcattc    60
agggattacc aatattgtgc tacctactgt attaacaaac aaaaaggaaa ctggtctcta   120
tgagaatccc tatgcggtgc cttcagagaa aacttcacca ggtttaaaga gaaaaacccct  180
gtctctacac ctccattccc agggcgagct cactctctgg catcaagttc cccgtgctca   240
gtttccctac acaagagtcc aagaggagag gtaaggagtg ggaggcaggg agtccagttc   300
agggacaggg attccaggac gagaagtgaa ggggaagggg ctgggcgcag cctgggggtc   360
tctccctggt ttccacagac agatccttgt ccaggactca ggcagacagt gtgacaaaga   420
ggcttggtgt aggagaagag ggatcaggac gaagtcccag gtcccggacg gggctctcag   480
ggtctcaggc tccgagggcc gcgtctgcaa tggggaggcg cacgttgggg attccccact   540
cccctgagtt tcacttcttc tcccaacttg tgtcgggtcc ttcttccagg atactcgtga   600
cgcgtcccca cttcccactc ccattgggta ttggatatct agagaagcca atcagcgtcg   660
ccgcggtccc agttctaaag tccccacgca cccacccgga ctcagag               707
```

<210> SEQ ID NO 44
<211> LENGTH: 1248
<212> TYPE: DNA
<213> ORGANISM: Homo sapiens

<400> SEQUENCE: 44

```
tttttttcccc ctagacatct cactctgtcg cccaggctgg agtgcagtgg tgtgatctcg    60
gctcactgca accaccacct ctcgggttca agcaattctc ctatctcagc ctccagagtt   120
gctggaatta caggcgcgca ccaccacacc cggctaattt ttgtattgtt agtagagaca   180
gggtttcatc atgttggcca ggttagtctt gaactcctga cctcgtgatc tgcctgcctc   240
ggcctaccaa aatgctgcga ttacaggcgt gagccaccgt tccggccta tacgttgttt   300
attttggaaa aattaaaaat taagtttttt ttcattaaag atatgttatt tccgatcaag   360
agatcaagac catcctggcc aacatggtga aaccccgtct ctactaaaaa cacaaaaatt   420
agctgggtgt ggtggcacac gcctgtagtt ccagttactg gggaggctga ggcaggagaa   480
tcgcttgaac ccgggagaag gaggttgcag tgagccgaga tcatgccact gcactccagc   540
ctggggacag agcaagactc tgactcaaaa aaaaaaaaag ttgtttctat taacatgtaa   600
tgggttatta atattctctt aaatgaatta atatttttaa tattttgttt taatatcttt   660
taatttatat atgataaaaa ttgatacaat ccacagaaac aaaatttatt tgggtcctca   720
ctaatttctt ttttcttgtt gcccaggctg gagggcaatg gcacgatctt ggctcaccgc   780
aacctcctcc tcctgggttc aagtgattct cctgcctcag cctcccaagt agccaggatt   840
acagccatgc gccaccacgc cggctaattt tttggacttt tagtagagac agggtttctc   900
catattggtc gggctggtct cgaactccca acctcaggtg atcagcccgc cttggcctcc   960
caaagtgctg agattacagg cgtgagccac cgcgcccagc caggactaat ttctaagagt  1020
gtgcagagat accgaaacct aaaagtttaa gaactgctga ttgctgggaa actctgcagt  1080
ttcccgttcc tctcgtaacc tggtcatgtg tccttcttcc tggatactca tgacgcagac  1140
tcagttctca ttcccaatgg gtgtcgggtt tctagagaag ccaatcagcg tcgccacgac  1200
tcccgactat aaagtccca tccggactca agaagttctc aggactca                1248
```

<210> SEQ ID NO 45
<211> LENGTH: 1245
<212> TYPE: DNA
<213> ORGANISM: Homo sapiens

<400> SEQUENCE: 45

```
cttccaagat ctctgcccct ccccatcgcc atggtccact tcctcttctc actgttcctc    60
ttagaaaaga tctgtggact ccaccaccac gaaatggcgg caccttattt atggtcactt   120
tagagggtag gttttcttaa tgggtctgcc tgtcatgttt aacgtccttg ctgggtcca    180
aggcagatgc agtccaaact ctcactaaaa ttgccgagcc ctttgtcttc cagtgtctaa   240
aatattaatg tcaatggaat caggccagag tttgaattct agtctcttag cctttgtttc   300
ccctgtccat aaaatgaatg ggggtaattc tttcctccta cagtttattt atatattcac   360
taattcattc attcatccat ccattcgttc attcggttta ctgagtacct actatgtgcc   420
agcccctgtt ctagggtgga aactaagaga atgatgtacc tagagggcgc tggaagctct   480
aaagccctag cagttactgc ttttactatt agtggtcgtt ttttctccc ccccgccccc    540
cgacaaatca acagaacaaa gaaaattacc taaacagcaa ggacataggg aggaacttct   600
tggcacagaa cttccaaac acttttttcct gaagggatac aagaagcaag aaaggtactc    660
tttcactagg accttctctg agctgtcctc aggatgcttt tgggactatt tttcttaccc   720
agagaatgga gaaaccctgc agggaattcc caagctgtag ttataaacag aagttctcct   780
tctgctaggt agcattcaaa gatcttaatc ttctgggttt ccgttttctc gaatgaaaaa   840
tgcaggtccg agcagttaac tggctggggc accattagca agtcacttag catctctggg   900
gccagtctgc aaagcgaggg ggcagcctta atgtgcctcc agcctgaagt cctagaatga   960
gcgcccggtg tcccaagctg gggcgcgcac cccagatcgg agggcgccga tgtacagaca  1020
gcaaactcac ccagtctagt gcatgccttc ttaaacatca cgagactcta agaaaaggaa  1080
actgaaaacg ggaaagtccc tctctctaac ctggcactgc gtcgctggct tggagacagg  1140
tgacggtccc tgcgggcctt gtcctgattg gctgggcacg cgtttaatat aagtggaggc  1200
gtcgcgctgg cgggcattcc tgaagctgac agcattcggg ccgag              1245
```

<210> SEQ ID NO 46
<211> LENGTH: 822
<212> TYPE: DNA
<213> ORGANISM: Homo sapiens

<400> SEQUENCE: 46

```
taggctttgc ccattatact ctctcatatt cattgacctg aatcctcaaa tgaggtgtgt    60
ccattagtca actccaatct cttgtcatat ataagatggt agagatgaga agaaggtagc   120
tcctttacag cccactattt ccactaacta ctacctgtgt ttcaagatac agcctttcat   180
ccttctccag tgttgagagt gttgaacctc agagtttctc ctctcatttt ctctaaatga   240
gatacaatgc cagccatccc aagctcttgg cctgagttgt tcatcttgaa gtctaggact   300
ccaagaagca tgaaagagct tctttagtga agctatgtcc tcagtactgc caaaattcag   360
acaatctcca tggcctgaca atttaccttc tatttgggta atttattgtc ccttacgcaa   420
actctccagc tgtcatggca cagacatatg atctgtattt agctctcact ttaggtgttt   480
ccattgattc tattctcact aatgtgcttc aggtatatcc ctgtctagaa gtcagattgg   540
ggttaaagag tctgtccgtg attgactaac agtcttaaat acttgatttg ttgttgttgt   600
tgtcctgttt gtttaagaac tttacttctt tatccaatga acggagtatc ttgtgtcctg   660
```

```
gaccctttgc aagaaccctt cccctagcaa cagatgcgtc atctcaaaat atttttctga    720
ttggccaaag agtaattgat ttgcatttta atggtcagac tctattacac cccacattct    780
cttttctttt attcttgtct gttctgcctc actcccgagc tc                       822
```

We claim:

1. A lentiviral expression vector comprising:
   (i) 300-1100 nucleotides of an MHC class I, MHC Class II, or β2 microglobulin upstream promoter sequence, and
   (ii) a transgene sequence under control of an MHC class I or β2 microglobulin promoter,
   wherein the MHC class I, MHC Class II, or β2 microglobulin upstream promoter sequence is selected from the group consisting of a β2 microglobulin upstream promoter sequence, an HLA-A2 upstream promoter sequence, HLA-B7 upstream promoter sequence, an HLA-E upstream promoter sequence and an HLA-DRα upstream promoter sequence.

2. The lentiviral vector of claim 1, comprising 300-600 nucleotides of an MHC class I or β2 microglobulin upstream promoter sequence.

3. The lentiviral vector of claim 1, comprising 300-400 nucleotides of an MHC class I or β2 microglobulin upstream promoter sequence.

4. The lentiviral vector of claim 1, wherein the upstream promoter sequence is in the same orientation as the MHC class I or β2 microglobulin promoter.

5. The lentiviral vector of claim 1, wherein the upstream promoter sequence is an MHC class I upstream promoter sequence selected from the group consisting of an HLA-A2 upstream promoter sequence, an HLA-B7 upstream promoter sequence and an HLA-E upstream promoter sequence.

6. The lentiviral vector of claim 1, wherein the upstream promoter sequence is a β2 microglobulin upstream promoter sequence.

7. The lentiviral vector of claim 6, wherein the upstream promoter sequence comprises the nucleotide sequence of SEQ ID NO:1 or SEQ ID NO:27.

8. The lentiviral vector of claim 1, wherein the promoter is an MHC class I promoter.

9. The lentiviral vector of claim 1, wherein the promoter is a β2 microglobulin promoter.

10. An isolated host cell comprising the lentiviral vector of claim 1.

11. The lentiviral vector of claim 1, wherein the upstream promoter sequence comprises the nucleotide sequence of any one of SEQ ID NO:2, SEQ ID NO:3, SEQ ID NO:4, SEQ ID NO:5, SEQ ID NO:6, SEQ ID NO:7, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

12. A method for producing the lentiviral expression vector of claim 1 comprising inserting 300-1100 nucleotides of an MHC class I, MHC Class II, or β2 microglobulin upstream promoter sequence into a lentiviral vector,
wherein the MHC class I, MHC Class II, or β2 microglobulin upstream promoter sequence is selected from the group consisting of a β2 microglobulin upstream promoter sequence, an HLA-A2 upstream promoter sequence, HLA-B7 upstream promoter sequence, an HLA-E upstream promoter sequence and an HLA-DRα upstream promoter sequence,
and wherein the lentiviral vector comprises a transgene sequence under control of an MHC class I or β2 microglobulin promoter.

13. The method of claim 12, comprising inserting 300-600 nucleotides of an MHC class I or β2 microglobulin upstream promoter sequence into a lentiviral vector.

14. The method of claim 12, comprising inserting 300-400 nucleotides of an MHC class I or β2 microglobulin upstream promoter sequence into a lentiviral vector.

15. The method of claim 12, wherein the upstream promoter sequence is inserted in the same orientation as the MHC class I or β2 microglobulin promoter.

16. The method of claim 12, wherein the upstream promoter sequence is an MHC class I upstream promoter sequence selected from the group consisting of an HLA-A2 upstream promoter sequence, an HLA-B7 upstream promoter sequence and an HLA-E upstream promoter sequence.

17. The method of claim 12, wherein the upstream promoter sequence is a β2 microglobulin upstream promoter sequence.

18. The method of claim 17, wherein the upstream promoter sequence comprises the nucleotide sequence of SEQ ID NO:1 or SEQ ID NO:27.

19. The method of claim 12, wherein the promoter is an MI-IC class I promoter.

20. The method of claim 12, wherein the promoter is a β2 microglobulin promoter.

21. The method of claim 12, wherein the upstream promoter sequence comprises the nucleotide sequence of any one of SEQ ID NO:2, SEQ ID NO:3, SEQ ID NO:4, SEQ ID NO:5, SEQ ID NO:6, SEQ ID NO:7, SEQ ID NO:28, SEQ ID NO:29, SEQ ID NO:30, SEQ ID NO:31, SEQ ID NO:32, SEQ ID NO:33, SEQ ID NO:34, SEQ ID NO:35, or SEQ ID NO:36.

* * * * *